(12) United States Patent  
Yang

(10) Patent No.: US 6,483,585 B1  
(45) Date of Patent: Nov. 19, 2002

(54) INSTRUMENTS FOR ANALYZING BINDING ASSAYS BASED ON ATTENUATION OF LIGHT BY THIN FILMS

(75) Inventor: Shao Yang, Superior, CO (US)

(73) Assignee: Thermo Biostar, Inc., Louisville, CO (US)

( * ) Notice: Subject to any disclaimer, the term of this patent is extended or adjusted under 35 U.S.C. 154(b) by 64 days.

(21) Appl. No.: 09/633,036

(22) Filed: Aug. 4, 2000

Related U.S. Application Data

(60) Provisional application No. 60/147,682, filed on Aug. 6, 1999.

(51) Int. Cl.[7] ................................................ G01J 4/00
(52) U.S. Cl. ..................................................... 356/369
(58) Field of Search ................................ 356/369, 364, 356/365, 366, 367, 368, 381, 382, 371, 237.1, 630; 250/372, 225

(56) References Cited

U.S. PATENT DOCUMENTS

| | | | | |
|---|---|---|---|---|
| 3,985,447 A | * | 10/1976 | Aspnes ........................ 356/118 |
| 4,606,641 A | * | 8/1986 | Yamada et al. .............. 356/369 |
| 4,695,162 A | * | 9/1987 | Itonaga et al. ............... 356/369 |
| 4,906,844 A | * | 3/1990 | Hall ............................. 250/225 |
| 5,076,696 A | * | 12/1991 | Cohn et al. .................. 356/369 |
| 5,333,052 A | * | 7/1994 | Finarov ........................ 356/369 |
| 5,420,680 A | * | 5/1995 | Isobe et al. .................. 356/128 |
| 5,450,201 A | * | 9/1995 | Katzir et al. ................. 356/369 |
| 5,494,829 A | * | 2/1996 | Sandstrom et al. .......... 436/518 |
| 5,517,032 A | * | 5/1996 | Imani ........................... 250/372 |
| 5,517,312 A | * | 5/1996 | Finarov ........................ 356/386 |
| 5,631,171 A | * | 5/1997 | Sandstrom et al. .......... 436/518 |
| 5,729,343 A | * | 3/1998 | Aiyer ........................... 356/355 |
| 6,278,519 B1 | * | 8/2001 | Rosencwaig et al. ........ 356/369 |

* cited by examiner

Primary Examiner—Michael P. Stafira  
(74) Attorney, Agent, or Firm—Foley & Lardner

(57) ABSTRACT

A modified and improved polarizier ellipsometer allows for improved signal quality and signal to noise performance. This improvement is based on rotating one polarizer relative to the other fixed polarizer to generate AC mode signals related to a thin film under analysis. The AC mode signal may be compared to a background signal and the ratio of sample signal to background signal used to provide a more accurate assessment of film thickness. The normalized AC signal for an unknown thickness may be compared to a standard curve generated for a film of similar optical properties for an exact thickness determination or may be used directly to report a relative thickness value. Other modifications of the improved polarizer ellipsometer of the invention are also described where one or both of the fixed polarizers are removed to improve the signal intensity through reduction of the number of optical components. These modifications are designed to address specific thin film and substrate combinations.

70 Claims, 11 Drawing Sheets

US 6,483,585 B1

INSTRUMENTS FOR ANALYZING BINDING ASSAYS BASED ON ATTENUATION OF LIGHT BY THIN FILMS

This application is related to and claims priority from U.S. provisional patent application No. 60/147,682, filed on Aug. 6, 1999, which is hereby incorporated by reference in its entirety, including all claims, figures, and tables.

INTRODUCTION

This invention pertains to instruments of simple design and operation used to measure the thickness of thin films as a function of changes to or attenuation of incident light. The devices and methods of this invention are improvements of a fixed polarizer ellipsometer where film thickness can be related as a function of the degree of ellipticity in polarized light, or rotation of polarized light, that is reflected by a thin film. More specifically, the invention relates to improvements in ellipsometry that speed measurement acquisition time and reduce the cost of ellipsometry devices for use in specific binding assays and other applications. The invention also relates to instruments and methods where measurement of light attenuation by a thin film is no longer dependent on the generation of elliptically polarized light.

BACKGROUND OF THE INVENTION

The following description of the background of the invention is provided simply as an aid in understanding the invention and is not admitted to describe or constitute prior art to the invention.

Optical measurements are commonly used to determine the thickness of thin films. Ellipsometers provide this information by determining the degree of ellipticity in polarized light that is reflected from a thin film. Ellipsometers typically include a light source, a polarizer, an analyzer, an optical compensator or quarter wave plate, and a detector. For example, U.S. Pat. No. 5,936,734 discloses using singly, partially, and/or multiply polarized electromagnetic radiation for ellipsometrically measuring regions of a patterned sample system, while U.S. Pat. No. 5,946,098 discloses a modified ellipsometer comprising a retarder element in the form of a prism.

Complex mathematical calculations are conventionally used to determine the film thickness. To use these mathematical calculations, the ellipsometer must have precise alignment of the rotating components for the measurement of signal intensity at the detector. Expensive and precise optical components must be used to provide for optimization of the detector signals in performing film thickness measurements. Measurement time is slow but the ellipsometer can provide precise thickness and refractive index determinations.

The rotation of ellipsometer components can be used to provide a sinusoidal plot of intensity at the detector as a function of time and angular velocity of the rotating component, as disclosed in U.S. Pat. No. 5,581,350. Measurements are made at two or more analyzer angles to determine the angle of the polarizer's optical axis and the offset of the actual analyzer angle relative to its nominal angle. Measurements provide the angle of the analyzer's optical axis and the offset of the polarizer angle relative to its nominal angle. This information is used to calibrate the ellipsometer, but the device operates according to time-consuming traditional principles that require precise alignment of rotating components for purposes of measuring film thicknesses. Similarly, U.S. Pat. No. 5,877,859 discloses rotating compensator ellipsometry methods, relying on a rotating compensator to produce a signal having a dc component, a two omega component, and a four omega component.

According to U.S. Pat. No. 3,985,447 it is also possible to rotate both the optical compensator and the polarizer at different angular speeds to measure the resultant transmitted optical intensity as a function of time. A Fourier analysis is used to determine the Stokes parameters of light that is reflected by the thin film. The film thickness and refractive index of the film can also be calculated in this manner based upon the Stokes parameters. A disadvantage of this device is that the system requires additional components including a time dependent rotating compensator. These additional components increase the expense and complexity of the system.

U.S. Pat. No. 4,725,145 discloses an instrument and method of use for measuring the state of polarization. The instrument contains only a photodetector. The photodetector has a partially specular surface and is placed at an oblique angle relative to the incident light source. The light adsorbed by the photodetector generates an electrical signal that is detected and related to the polarization of the light. The detector may be rotated to determine if the light contained any elliptical character. In the preferred mode of operation the entire system is rotated. The improvement is that the instrument does not include any wave retarders or polarizers. The system may contain one or more photodetectors. The amount of light adsorbed is a fraction of the incident radiation and is dependent on the incident light source and the azimuthal orientation of the plane of incidence. The detector surface rotates in a conical manner. Thus the plane of incidence is a plane which revolves around and through the incident light. The electrical output is modulated by the rotation and thus the modulation is a measure of the state of polarization of the light incident on the detector.

U.S. Pat. No. 5,552,889 discloses a method for measuring changes in polarized light that is independent of temperature. The method examines the AC and DC components of the light separately. The method requires an instrument design where two or more polarizers are arranged so that they are not orthogonal to each other. The modulation of the polarized signal is then measured at one or more photodetectors. The intensity of a constant component of the polarization signal is related to the position of the average plane of polarization. The alternating component of the polarization signal is normalized to the constant component and then the phase, amplitude, and position of the polarization is determined. The polarization signal is exactly linearized. The method requires a beam splitter to produce two beams of light.

U.S. Pat. No. 5,625,455 discloses an ellipsometer and an ellipsometric method. In the method the complex dielectric constant, the complex index of refraction, the transmittance, the reflectance, the adsorption coefficient, the optical density, and other optical properties may be measured by reflectance of a monochromatic light source. The instrument and method of use provide a direct measure of the optical and spectroscopic properties of the sample without numerical approximation or wavelength frequency scans. The light source should be elliptically polarized and the angle of incidence should be between 0° and 90°. The digitized intensity data reflected or transmitted from the sample is analyzed using integrals or sums. The integrals eliminate noise and allow the method to start and stop at any analyzer angle.

In certain applications, it is possible to eliminate some of the components from an ellipsometer-like device for purposes of reducing the cost of manufacture while still providing an acceptable level of accuracy. U.S. Pat. No. 5,494,829 to Sandstrom et al. describes a device that operates according to the principles of ellipsometry, but has a fixed polarizer and a fixed analyzer with the additional cost advantage of having no optical compensator or other complex optical components. This device is used for binding assay analysis to determine whether a biochemical reaction has provided a thin film analyte indicating the presence of bacterial infection in a patient.

According to the '829 patent, an antigen or an antibody is bound to a substrate and is incubated with an analyte solution that is prepared to include a body fluid specimen from a patient who is being tested for infection. A biochemical reaction grows a thin film on the substrate if the corresponding antibody or antigen is present in the solution. A positive test result is indicated by signal intensity at the detector relative to a delimiting threshold or background value. The device is typically calibrated to measure thickness in films having been produced by a particular antigenic reaction.

A number of spectrophotometric systems have been designed to analyze the thickness of films, in particular photoresist films. These instruments require complex arrangements of optical components or focus on specific geometric features in the film. The instruments may require detection of more than one wavelength or angle to determine the film thickness. Several of the methods will not work without exact information on the refractive index of the film. The spectrophotometers do not measure film thicknesses well on optical substrates with low reflectivity. The most significant limitation is the poor signal to noise ratio obtained with these instruments. These instruments also have difficulty measuring films such as amorphous silicon.

For example, U.S. Pat. No. 4,680,084 describes a very complicated instrument that uses multiple light sources and lens and beam splitters and more than one detector to determine the thickness of a film. In addition the method requires that the optical substrate have patterned features present that are opaque to the incident light. These features are used to correct the detected signal for contributions unrelated to the film thickness. U.S. Pat. No. 4,618,262 describes a laser-based interferometer that measures an etching process depth by the use of specific features on the optical substrate to determine when the etch process is complete. In this method the distance between adjacent maxima are used to determine the etching rate. The characteristic sinusoidal pattern terminates when the etch process reaches the optical substrate. This method must be able to resolve etch features on the order of 1–3 microns which is problematic because the laser beam is on the order of 700 microns in diameter. Thus resolution of these small features from background is difficult. Optical components have been added to the system to address this issue.

U.S. Pat. No. 5,494,829 describes the use of a simple calorimeter or reflectometer to measure a color change or a change in intensity for interpretation of binding assay results. The signal is a function of a change in wavelength or the change in intensity of a range of wavelengths where the optical substrate is designed to generate a visual interference effect and thus change color as a function of thickness change.

Each of the foregoing U.S. Patents describing the background of the invention is hereby incorporated by reference in its entirety, including all tables, figures, and claims.

There remains a need to provide inexpensive ellipsometric instruments that measure film thickness with acceptable accuracy for a variety of binding assays or other applications. This need may be addressed by ellipsometry, or other thin film mechanisms for light attenuation, where the device is capable of measurement without undue time being spent to align system components and without unnecessary optical components that reduce system efficiency. There also remains a need to provide inexpensive reflectometric instruments that measure film thickness with acceptable accuracy, without necessarily providing an absolute thickness determination, for a variety of binding assays and other applications according to the principles of multilayer film reflection theory. The reflectometric instruments should also be capable of performing measurements without undue time being spent to align system components, to acquire signals, or to analyze signals. The instruments of this invention are easy to operate and the data interpretation is straightforward. The instrument performance is highly predictable as the response to any particular binding assay system can be modeled and the instrumentation is tailored to analysis a particular binding assay surface construction or a range of similar constructions.

SUMMARY OF THE INVENTION

The invention provides devices and methods for use in measuring film thickness comprising an AC mode fixed polarizer ellipsometer. Use of the AC mode eliminates the need for the precise alignment of the polarizing elements, thus reducing the cost of manufacturing the device. In the AC mode, one of the polarization elements, e.g., the analyzer or the polarizer, is rotated in complete cycles at a constant speed in order to generate an alternating signal at the detector element. The device improves the signal over existing fixed angle polarizer ellipsometers because the change in signal versus the change in thickness produces a steeper slope (i.e., a larger signal difference for a change in thickness), and thus a better signal to noise ratio. As the analyzer or polarizer rotates, the signal received from a test surface varies with the rotation of the analyzer (polarizer), or varies as a function of time. The signal observed is thus a quasi-sinusoidal curve with an amplitude and phase that is characteristic of the film being analyzed. The data analysis can utilize any combination of features in the signal generated, but preferably uses a peak to peak difference as the output for a specific thin film. For instance, an average of all the peak signal strengths can be made and reported as the sample value. Exact thickness determinations can be made by comparison of the peak to peak value for an unknown sample relative to a standard curve of instrument output versus known film thicknesses. The standard curve is based on a film that is similar or identical in properties to the thin film to be analyzed and that is deposited on a substrate with the same structure as the substrate used with the test film. The standard curve can also be created by theoretical calculations. The AC mode ellipsometer is designed such that all instrument parameters are modeled to allow maximum thickness differentiation over a pre-determined range of thickness for a given optical support and thin film layer(s) combination.

Other instrument embodiments (reflectometric) involve the use of one polarizer or no polarizer, respectively, in the measurement of a change in the characteristics of light reflected from an optical substrate supporting one or more thin film. By eliminating one or both of the polarizers, the reflectometric instrument design is both less complex and less expensive. The removal of the polarizing elements also provides an advantageous increase in signal intensity, because any optical element will introduce some insertional loss of signal. The single polarizer instrument is preferably used when only one component (i.e., the s or p polarization component) of the incident light is to be used. In the single polarizer instrument either the polarizer or the analyzer may be removed.

Moreover, at a steep angle of incidence there is very little operational difference in the s- and p-components of light. Accordingly, if both components are used to measure film thickness, for example in a polarizer-free device, the instrument performs equivalently to a device comprising a polarization element. Thus, in other embodiments, the invention concerns polarizer-free devices which use unpolarized light at steep angles of incidence. The polarizer-free instrument is designed to analyze a specific optical substrate in order to measure a film created by the binding of a biological material, or a film created in other binding assays, over a range of film thicknesses. The thickness range to be accommodated depends on the type of binding assay to be performed. Based on empirical observation or theoretical calculations from thin film reflection theory, the proper wavelength of incident light and angle of incidence can be selected. Thus, a single instrument design can be selected that will accommodate a number of different binding assays based on a similar optical substrate.

In other preferred embodiments, the invention also provides methods of using any of the devices described herein to relate a change in light intensity to a change in film thickness. An exact thickness determination can be made by comparison to a standard intensity curve generated with known film thicknesses, where the standard curve is created with a known film that is optically similar to the test film. The detector signal intensity may be used without correction, or following correction using a comparative detector signal intensity (i.e., application of a normalizing function) obtained from a negative binding control sample, or other background measurement.

The present invention overcomes the problems known to those skilled in the art that are outlined above, and advances the art by providing cost-effective devices that measures film thickness with acceptable accuracy for a variety of binding assays and other applications according to the principles of ellipsometry. These advantages are obtained by rotating the analyzer or the polarizer to produce a quasi-sinusoidal intensity in reflected light from the sample under test and by mapping selected intensity values to a film thickness through the use of a standard curve or other reference data. This concept permits the devices described herein to perform film thickness measurements without undue time being spent to align system components and without the use of complex mathematics and optical components. The system is inexpensive to manufacture because it does not require the use of an optical compensator, quarter wave plate, or other precision optical components and component alignment.

Thus, in a first aspect, the invention describes devices for use in determining a film thickness of a sample. The devices can comprise a substrate for supporting the sample; a light source for producing electromagnetic radiation to illuminate the sample; a first polarization element located between the light source and the sample; a detector for detecting electromagnetic radiation reflected from the sample; and a second polarization element located between the detector and the sample. At least one of the first and second polarization elements can be rotated to vary an s and/or p content of the electromagnetic radiation with time. The signal obtained from the detector is used to determine film thickness by a method comprising the use of a standard function that correlates film thickness to detector signal intensity.

In particularly preferred embodiments, one or more of the following can be included in the devices: (i) a light source that produces monochromatic electromagnetic radiation, (ii) electromagnetic radiation selected from the group comprising visible light, infrared light, and ultraviolet light, (iii) a first polarization element comprising a rotatable polarizing filter, (iv) a second polarization element comprising a rotatable polarizing filter, (v) a first polarization element comprising a rotatable polarizing filter, and a second polarization element comprising a fixed analyzer, (vi) a first polarization element comprising a fixed polarizing filter, and a second polarization element comprising a rotatable analyzer, (vii) rotating at least one of the first and second polarization elements to provide a quasi-sinusoidal intensity signal at said detector, (viii) relating a film thickness to an amplitude of the quasi-sinusoidal intensity signal, (ix) relating a film thickness to a peak to peak amplitude of the quasi-sinusoidal intensity signal, (x) a control sample comprising a known film thickness, (xi) a control sample that is a negative control sample, (xii) a standard function comprising a normalizing function which relates the detector signal intensity to a comparative detector signal intensity obtained from the negative control sample, and (xiii) a normalizing function that is a ratio of the detector signal intensity and a comparative detector signal intensity obtained from the negative control sample.

The term "sample" as used herein refers to any material which can be deposited on the surface of a substrate to form a film. Preferred samples can be organic materials such as biological materials (e.g., nucleic acids, antibodies, antigens, receptors, analytes, chelators, enzyme substrates, etc.), or inorganic materials such as silicon oxide, silicon dioxide, silicon nitride, etc. A sample preferably can be a solution containing such materials. The term "negative control sample" as used herein refers to any substrate which lacks a thin film. Such a negative control sample can be used to provide a baseline or comparative signal from the device.

The terms "film" and "thin film" as used herein refer to a one or more layers of sample material deposited on a substrate surface. A film can be about 1 Å in thickness, about 5 Å in thickness, about 10 Å in thickness, about 25 Å in thickness, about 50 Å in thickness, about 100 Å in thickness, about 200 Å in thickness, about 350 Å in thickness, about 500 Å in thickness, about 750 Å in thickness, about 1000 Å in thickness, and about 2000 Å in thickness. Particularly preferred are films from about 5 Å to about 1000 Å; most preferred are films from about 5 Å to about 350 Å.

The terms "substrate," "optical support" and "support" as used herein refer to a support within a device for a sample under study. Suitable substrates can be made of any reflective material known by those skilled in the art, and provide a planar surface upon which a sample film is deposited. Preferably, the substrate is a polished silicon wafer, alumina, or glass or a material coated with one or more of these materials. For example, a substrate may be a polycarbonate membrane coated with a layer of amorphous silicon, a fibrous material coated with aluminum or chromium and an optical layer of amorphous silicon, or a ceramic coated with a layer of metal and/or amorphous silicon. The primary consideration for selection of the substrate is the reflectivity of the material and/or its ability to be coated with a reflective material.

The term "optical pathway" as used herein refers to a pathway within a device through which electromagnetic radiation may pass. The optical pathway serves to direct electromagnetic radiation from a light source to a sample under study, and ultimately to a detector that measures one or more properties (e.g. intensity, polarization, etc.) of light that is reflected by the sample. The optical pathway may contain various elements of the device, such as polarization elements that are positioned to polarize incoming electromagnetic radiation from the light source prior to contact with the sample under study, and/or electromagnetic radiation reflected from the sample under study. The optical pathway preferably includes only those components that are required to permit the detector to provide signals that facilitate qualitative measurements of film thickness. Such devices can be cost-effectively deployed for applications where ellipsometers have not been traditionally used, for example, in the physician's office.

The term "light source" as used herein refers to any source of electromagnetic radiation. Electromagnetic radiation can also be referred to as "light." Such electromagnetic radiation may include wavelengths from about $10^{-6}$ μm to about $10^8$ μm, preferred is electromagnetic radiation from the ultraviolet to infrared wavelengths; particularly preferred electromagnetic radiation is visible light. Suitable light sources are well known to those skilled in the art, and can include any source of monochromatic or polychromatic radiation. The use of monochromatic radiation is preferred. The terms "monochromatic radiation" or "monochromatic" light as used herein refer to electromagnetic radiation having a bandwidth that is sufficiently narrow to function as a single wavelength for design purposes. Preferred light sources are lasers, laser diodes, and light emitting diodes.

As used herein, the term "detector" refers to any device for detecting electromagnetic radiation by the production of electrical or optical signals, and includes photomultipliers, photodiodes, and photochemical reagents, whether these detectors are driven to provide analog or digital signals, as well as any other light detection device. Preferred detectors detect electromagnetic radiation, particularly visible light, with the resulting production of electrical or optical signals. A signal processing element can process these signals to yield this information, for example by the use of standard curves, to associate the signals with a film thickness. In especially preferred embodiments, the film thickness is interpreted as a binding assay result, e.g., the result of a test showing either a positive, negative, or inconclusive result in a test for a specific analyte.

The term "polarization element" as used herein refers to a device that receives incoming electromagnetic radiation, and produces therefrom radiation which is polarized. Suitable polarization elements, such as polarizing filters and analyzers, are well known to those skilled in the art. As described herein, polarization elements can be positioned to polarize incoming light from the light source prior to contact with the sample under study, as well as light reflected from the sample under study. A polarization element can be fixed within the optical pathway. Alternatively, one or more of the polarization elements can include a mechanism for varying s- and p-components of polarized light with time by rotating the polarization element, or a component thereof, on its optical axis. Preferably, this mechanism rotates a polarizing filter that is located in the position of a polarizer or analyzer in a conventional ellipsometer. Rotation of a polarizing filter provides a corresponding quasi-sinusoidal intensity in the electromagnetic radiation that is reflected from the sample under study.

The term "linear polarization" as used herein refers to a polarization state that is essentially all s-polarization or all p-polarization. Electromagnetic radiation is linearly polarized if, in either linear state, there is not enough of the other polarization state to affect the outcome of the measurement. Preferably, a linear polarizing filter may be rotated up to about 20° rotation off of its optical axis without introducing appreciable measurement errors; more preferably, this rotation is limited to less than about 10°; even more preferably, limited this rotation is limited to less than about 5°, with a precise alignment of about 1° or less being most preferred.

In another aspect, the invention concerns methods of measuring a film thickness of a sample. The methods can comprise providing a device comprising a light source, a polarizer, an analyzer, and a detector; directing electromagnetic radiation from the light source towards the sample, whereby electromagnetic radiation is reflected from the sample; polarizing the electromagnetic radiation that is directed towards the sample using the polarizer; polarizing the electromagnetic radiation reflected from the sample using the analyzer; rotating the polarizer or the analyzer to vary the s and p content of the polarized electromagnetic radiation with time; detecting the polarized electromagnetic radiation reflected from the sample using the detector to obtain a signal corresponding to the intensity of the reflected electromagnetic radiation; and correlating the signal to the film thickness of the sample using a standard function that relates film thickness to detector signal intensity. Other data analysis means can be used as known to those skilled in the art.

In particularly preferred embodiments, one or more of the following may be included in the methods: (i) a standard function selected from a plurality of standard functions obtained from samples having different optical properties, (ii) a comparative detector signal intensity obtained from a negative control sample, (iii) a standard function comprising a normalizing function which relates the detector signal intensity to the comparative detector signal intensity, (iv) a normalizing function that is a ratio of the detector signal intensity and the comparative detector signal intensity, and (v) a polarizer or an analyzer that provides a corresponding quasi-sinusoidal signal from the detector.

Selected signals can be obtained in a time domain corresponding to predetermined degrees of rotation of the polarizing filter, or other polarization element, which varies the s and p content of the polarized light. These intensity signals are used as input to generate a standard function, e.g., standard curves of empirical or theoretical data that relate film thickness as a function of the magnitude of detector signal intensity through a range of polarizing rotation. Any mapping technique may be used to relate or map the intensity corresponding to a particular degree of rotation with a film thickness. These other mapping techniques may include, without limitation, neural networks and adaptive filters, which are all referred to in the context of this application as "standard functions".

A particular advantage that derives from the ellipsometric embodiments of the invention is that operation of the device does not require time consuming positional adjustment of the polarization element in order to optimize intensity in signals from the detector. More particularly, measurement data can be collected from all points in the cycle of polarizing rotation and used to establish a peak to peak amplitude of the quasi-sinusoidal signal. This peak to peak amplitude is used as input into the standard curve in order to determine film thickness.

A particularly preferred feature of the ellipsometric embodiments is the use of a normalizing function that expresses the detector signal intensity in relationship to a comparative detector signal intensity obtained from a negative control sample. This normalizing function is most preferably a ratio between the detector signal intensity and the comparative signal intensity from the negative control sample, e.g., the detector signal intensity divided by the intensity of the signal from the negative control sample.

In another aspect, the invention concerns devices for use in interpreting thin film binding assays which comprise a substrate for supporting a sample; a light source for producing electromagnetic radiation to illuminate the sample; a detector for detecting electromagnetic radiation reflected from the sample; an optical pathway between the light source, the sample, and the detector; and a signal processor for correlating the signal with a film thickness on the sample. The optical pathway comprises a fixed polarization element located between the sample and the detector to linearly polarize the reflected electromagnetic radiation. A signal produced by the detector corresponds to the intensity of the electromagnetic radiation reflected from the sample.

In particularly preferred embodiments, one or more of the following can be include d in the device: (i) a light source that produces monochromatic electromagnetic radiation, (ii) electromagnetic radiation preferably selected from the group comprising visible light, infrared light, and ultraviolet light, (iii) linearly polarized electromagnetic radiation that is essentially s- or p-polarized relative to a plane of incidence in the optical pathway between the polarizer and the detector, (iv) relating a film thickness to a thin film binding assay result, and (v) an optical pathway comprising a single polarization element.

In another aspect, the invention concerns methods of measuring a film thickness of a sample which comprise providing a device comprising a light source, a detector, a first optical pathway between the light source and a sample, and a second optical pathway between the sample and the detector; directing electromagnetic radiation from the light source along the first optical pathway to the sample, such that electromagnetic radiation is reflected by the sample along the second optical pathway to the detector; linearly polarizing the electromagnetic radiation along the first optical pathway at a position prior to contact of the electromagnetic radiation with the sample; detecting the electromagnetic radiation reflected by the sample using the detector to obtain a signal corresponding to the intensity of the reflected electromagnetic radiation; and correlating the signal to the film thickness of the sample.

In particularly preferred embodiments, one or more of the following can be included in the methods: (i) linearly polarized electromagnetic radiation that is essentially s- or p-polarized relative to a plane of incidence in the second optical pathway between the polarizer and the detector, (ii) relating a film thickness to a thin film binding assay result, and (iii) performing the method without polarization of the electromagnetic radiation reflected from the sample.

In another aspect, the invention concerns methods of measuring a film thickness of a sample which comprises providing a device comprising a light source, a detector, a first optical pathway between the light source and a sample, and a second optical pathway between the sample and the detector; directing electromagnetic radiation from the light source along the first optical pathway to the sample such that electromagnetic radiation is reflected by the sample along the second optical pathway to the detector; linearly polarizing the electromagnetic radiation along the second optical pathway at a position after contact of the electromagnetic radiation the said sample; detecting the electromagnetic radiation reflected by the sample using the detector to obtain a signal corresponding to the intensity of the reflected electromagnetic radiation; and correlating the signal to the film thickness of the sample.

In particularly preferred embodiments, one or more of the following can be included in the methods: (i) linearly polarized electromagnetic radiation that is essentially s-or p-polarized relative to a plane of incidence in the second optical pathway between the polarizer and the detector, (ii) relating a film thickness to a thin film binding assay result, and (iii) performing the method without polarization of the electromagnetic radiation prior to reflection from the sample.

An optical pathway according to the invention includes specific combinations of elements that operate according to the principles of multiple thin-film reflection theory. In a preferred embodiment, the optical pathway comprises a polarizing filter that is positioned to linearly polarize light prior to its illumination of the sample under study. In other preferred embodiments, the optical pathway comprises a polarizing filter that is positioned to linearly polarize light that is reflected from the sample under study.

In these two instrument configurations, the polarization element, either in the path of the incident electromagnetic radiation or in the path of reflected electromagnetic radiation, is used to select one component of the polarized electromagnetic radiation, i.e., either the s- or the p-component. When the polarizing element is in the path of the incident electromagnetic radiation, the s- or p-polarized electromagnetic radiation is incident on the sample under study. Upon interaction with the sample under study, the electromagnetic radiation undergoes an amplitude change relative to electromagnetic radiation that has reflected from a sample under study without the added thin film, e.g. relative to a negative control sample. The reflected electromagnetic radiation is not elliptically polarized, and there is no change in the degree of polarization. Rather, there is only an attenuation of the light relative to the light that is reflected from a sample that does not have an added thin film. A similar case is generated when the incident electromagnetic radiation, and thus the reflected electromagnetic radiation, is unpolarized. In such a case, a polarization element in the path of the reflected electromagnetic radiation will pass only one component of the electromagnetic radiation to the detector.

In another aspect, the invention concerns devices for use in interpreting thin film binding assays which comprises a substrate for supporting a sample, a light source for producing electromagnetic radiation to illuminate the sample, a detector for detecting electromagnetic radiation reflected from the sample, an optical pathway between the light source, the sample, and the detector, and a signal processor for correlating said signal with a film thickness on said sample. A signal produced by the detector corresponds to the intensity of electromagnetic radiation reflected from the sample.

In particularly preferred embodiments, one or more of the following can be included in the devices: (i) a light source that produces monochromatic electromagnetic radiation, (ii) electromagnetic radiation selected from the group comprising visible light, infrared light, and ultraviolet light, (iii) a light source positioned relative to the sample and the detector to provide a low angle of incidence, (iv) an optical pathway comprising neither a polarizer located between the light source and the sample, nor a polarizer located between the sample and the detector, (v) a light source positioned at an angle of incidence ranging from about 0° to about 30°, determined relative to a line normal to the plane of the sample, (vi) a light source positioned at an angle of incidence ranging from 0° to 20°, (vii) a light source positioned at an angle of incidence ranging from 0° to 10°, (viii) relating a film thickness to a thin film binding assay result, (ix) an optical pathway comprising a polarizing filter which provides circularly polarized light, (x) a polarizing filter located in the optical pathway between the light source and the sample, and (xi) a polarizing filter located in the optical pathway between the sample and the detector.

In another aspect, the invention describes a method of measuring a film thickness of a sample which comprises providing a device comprising a light source, a detector, a first optical pathway between the light source and a sample, and a second optical pathway between the sample and the detector; directing electromagnetic radiation from the light source along the first optical pathway to the sample such that electromagnetic radiation is reflected by the sample along the second optical pathway to the detector; detecting the electromagnetic radiation reflected by the sample using the detector to obtain a signal corresponding to the intensity of the reflected electromagnetic radiation; and correlating the signal to the film thickness of the sample. Preferably, the electromagnetic radiation is unpolarized at said detector without movement of components in said optical pathway.

In particularly preferred embodiments, one or more of the following can be included in the method: (i) a light source positioned at a low angle of incidence determined relative to a line normal to the sample, (ii) an optical pathway comprising neither a polarizer located between the light source and the sample, nor a polarizer located between the sample and the detector, (iii) a low angle of incidence ranging from about 0° to about 30°, (iv) a low angle of incidence ranging from 0° to 20°, (v) a low angle of incidence ranging from 0° to 10°, and (vi) relating a film thickness to a thin film binding assay result.

In these preferred embodiments, the invention describes devices in which the light source and the detector are positioned in the device at angles of incidence where essentially unpolarized reflected light to the detector can be used. In this device configuration, the light source can be positioned at an angle of incidence ranging from about 0° to about 30°, determined relative to a line normal to the plane of the sample. Preferably, the angle of incidence can be about 0°, about 5°, about 10°, about 15°, about 20°, about 25°, or about 30°. The wavelength of the electromagnetic radiation to be provided can be determined empirically, using multilayer thin film reflection theory that is well known in the art. Using such theory, the selected wavelength is a function of the angle of incidence, the approximate thickness of the thin film on the sample under study, and the reflective surface that is used to support the thin film.

In any of the reflectometric embodiments, it is preferred to have no additional polarizing means other than those that are specifically mentioned. For example, in the first reflectometric embodiment where light is polarized prior to contact with the sample under study, it is preferred not to have a polarizing filter located between the sample and the detector. Similarly, in the second reflectometric embodiment where light is polarized after contact with the sample under study, it is preferred not to have a polarizing filter located between the sample and the light source. In the third reflectometric embodiment, it is preferred not to have any polarizing filters.

The most cost effective devices described in the invention simply mount a light source on a housing or frame that positions the light source relative to the substrate and the detector in a manner providing a suitable angle of incidence. Reflected light from the substrate arrives at the detector relative to the incident light or light that is reflected from the surface without a thin film. In this case, the light source is a monochromatic light source and the combination of elements includes neither a polarizer located between the light source and the sample under study nor an analyzer located between the sample under study and the detector.

A particular advantage of the present invention is that operation of the reflectometric embodiments do not require positional adjustment of the polarization elements. Removing one or more of the polarizing elements from the instrument's optical path increases the amount of light available to the detector. Thus, the instrument is more sensitive than conventional instruments, where light is lost by passage through the polarizing elements. More particularly, measurement data is collected as a detector signal intensity that is compared to a delimiting value. This delimiting value is associated with a background or negative test result or other indicator of film thickness change. In its most fundamental form, the interpretation of test results is essentially an answer of yes or no, positive or negative, based upon signal intensity measurements showing the presence or absence of a thin film or the presence of a film with a thickness greater than a preselected threshold thickness. In such a preferred embodiment, actual film thickness does not need to be calculated, provided the test results conclusively establish the presence or absence of such a film. Because the signal is a function of the film thickness, and the film thickness is a function of analyte concentration in a sample, the instrument can also provide a quantitative determination of analyte concentration without an absolute determination of the film thickness.

It is also contemplated that the test interpretation could include a third indicator, namely, an indicator that the test is inconclusive because the signal intensity falls within a range of values between a definite negative and a definite positive.

In addition to assays where direct detection of analyte binding results in an increase in thickness on the thin film support, assays where a decrease in thickness or where the analyte concentration is inversely related to signal can be envisioned. Examples of such assays would include enzymatic degradation of the thin film surface where the substrate is specific to an enzyme as the analyte of interest or a competitive assay where the analyte competes with the amplifying reagent and the thickness change decreases with increasing analyte concentration.

Also instrument response to a change in thickness can be an increase in light intensity to the detector or a decrease in light intensity to the detector.

DETAILED DESCRIPTION OF THE PREFERRED EMBODIMENTS

AC-mode Instruments

Figure 1:
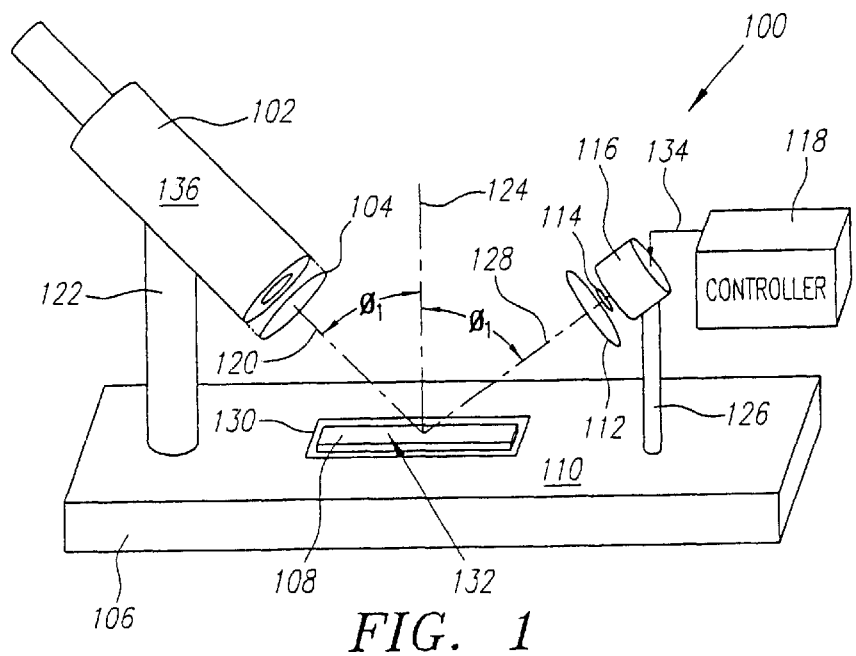
FIG. 1 depicts an AC mode thin film-analyzing instrument according to the present invention where one of polarizing elements is rotated.

FIG. 1 is a schematic diagram of a thin film-analyzing instrument 100 according to the present invention. A light source 102 is mounted in fixed relationship with respect to a first polarizing filter or polarizer 104 and a support base 106. A film-bearing substrate 108 rests on support surface 110. A rotating analyzer, i.e., a second polarizing filter 112, is coupled or integrally formed with a detector 114. A possible instrument configuration involves the combined assembly including second polarizing filter and detector 114, where the analyzer is rotated by a stepper motor 116 however this is a less desirable configuration. A controller 118 governs the rotation of stepper motor 116 and receives signals from detector 114.

Light source 102 can be any source of electromagnetic radiation, including a polychromatic or monochromatic light source, but is preferably a monochromatic light source, such as a laser, laser diode, or LED. Light source 102 discharges light along a first optical pathway segment 120 to illuminate the film-bearing substrate 108. Light on this first optical pathway segment 120 is polarized by action of the first polarizing element 104, which is preferably a linear polarizing filter.

Mounting base 106 includes a first pillar 122, which selectively retains light source 102 to transmit light in a manner such that first optical pathway segment 120 is at an angle $\phi_1$ representing a departure from a normal line 124 taken with respect to substrate 108. The first optical pathway segment 120 can include a narrow beam of light or a wider body of collimated light. In either case, first optical pathway segment 120 exists at the center of the beam. Selective adjustments may be made by a pair of perpendicular set screws, a ball-pivot friction clamp or any other conventional selective adjustment mechanism (none depicted in FIG. 1). A second pillar 126 provides a similar adjustment mechanism (not depicted in FIG. 1) to center the assembly including stepper motor 116, detector 114, and second polarizing filter 112, along a second optical pathway segment 128. This second optical pathway segment 128 departs from vertical also by angle $\phi_1$. A basin or well 130 is formed within surface 110 for positional alignment of substrate 108 with respect to first and second optical pathway segments 120 and 128.

The detector 114 is selected to detect light in wavelengths corresponding to the light that is emitted by light source 102 and reflected by test surface 132. The detector provides signals that represent the intensity of light at the detector in any units supported by the electronics of the system. Detector 114 transmits these signals to controller 118 on cable 134, and controller 118 interprets these signals to determine a film thickness. Controller 118 also governs the rotation of stepper motor 116, which rotates analyzer 112 on its optical axis. It is also possible to eliminate stepper motor 116 and rotate analyzer 112.

It will be appreciated that the housing 136 of light source 102 may optionally contain a stepper motor similar to stepper motor 116, and that this motor may be actuated by instructions from controller 118. Thus, either the polarizer 104 or the analyzer 112 may be rotated for purposes of the invention. Because one of the polarizing elements is rotating the precise alignment of the two polarizing elements is not required as in the prior art fixed polarizer instrument.

In the AC mode instrument of FIG. 1, light of varying polarization states is generated. The changing polarization states of the light may be incident on the surface to be analyzed when polarizer 104 is rotated. Or light that is reflected from the surface may be sorted by polarization state when the analyzing polarizer is rotated (polarizer 112). In either case, the polarization state of the light incident on the thin film is also altered by passage and reflection of the light from the interfaces at the substrate/thin film and at the thin film/air interface. The attenuation of the polarization state and thus the intensity of light reflected from the surface is a function of the angle of incidence within the film and the film thickness. For this discussion a single thin film composition is assumed. A multi-layer thin film can also be used in the instrument by using an assumption that each film's reflected light adds to the light reflected from the film interface above it. The combined product is the light that is reflected to the next layer or to the detector. The signal from a test surface is collected as a function of the polarizer rotation instead of a fixed, direct measurement used in the fixed polarizer prior art instrument. The rotation of the polarizer generates a signal that is quasi-sinusoidal in nature and allows for peak to peak information to be collected. The change in signal from peak to peak is a function of the thickness of the film. As either one of these values is larger than the direct measurement made from the same film, the AC operation of the instrument improves instrument sensitivity and accuracy. An added advantage is that the AC measurement is free from the 1/f noise present in optical detectors and electronic amplifiers at very low frequencies. This decrease in noise along with the increase in thickness sensitivity improves the resolution of the instrument relative to conventional instruments. In addition the devices of the invention do not need to determine the actual phase of the reflected light, as in conventional ellipsometry, but only require the analysis of the intensity of the reflected light. The instruments of this invention do not need to determine the phase of the light to provide a determination of film thickness.

The angle of incidence and the wavelength of incident light is selected based on the optical properties, refractive index, reflectivity, etc, of the optical substrate used to support the thin films of the binding assay. These instrument settings are also influenced by the range of thicknesses likely to be encountered in the binding assay. These parameters can be modeled using a number of thin film reflection theory software packages.

AC-mode Methods

Figure 2:
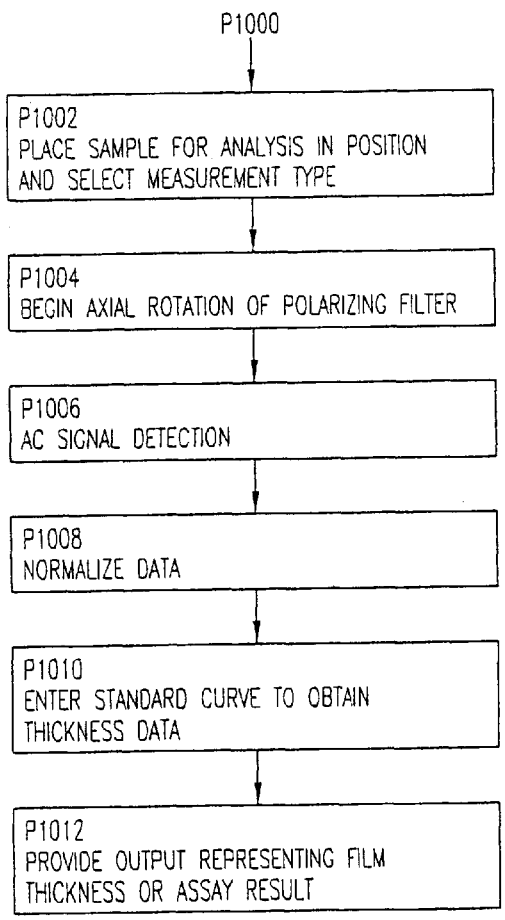
FIG. 2 depicts the analysis flow chart used with an AC mode thin film-analyzing instrument.

The process of using the instrument of FIG. 1 follows the flow diagram of FIG. 2. The process P1000 begins with step P1002 in which a user places a sample for analysis in the instrument 100. This placement corresponds to placing substrate 108 in well 130. At this time, a keypad or other input device is used to select a type of assay that the equipment is calibrated to perform, e.g., to select from between binding assays. Examples of binding assays include immunoassays for Human Immunodeficiency Virus, (HIV) I or II or a combination thereof, Streptococcus Group A, Streptococcus Group B, Respiratory Syncitial virus, Hepatitis B, a Chlamydia species, and Herpes Simplex virus.

Step P1004 commences axial rotation of a polarizing filter. These filters include the polarizer 104 and the analyzer 112, but in any one instrument configuration only one polarizing element is rotated.

The rotation of step P1004 produces an alternating or quasi-sinusoidal $I_{out}$ detector signal. The peak to peak value of these signals is read by conventional analog or digital methods.

Step P1008 involves normalizing the signal intensity values that are obtained in step P1006. This normalization is performed, as described above, by dividing the intensity signal with a corresponding intensity signal that is obtained over the same cycle of rotation with respect to a sample of known thickness, e.g., a negative control or background sample. Normalization is accomplished by dividing the peak to peak value for the negative control sample into the peak to peak value for the sample under study. The overall analysis time will depend on the number of cycles measured and used in the data analysis. As the number of cycles increases the accuracy of the result will improve, however, as the instrument is designed to provide rapid results the number of cycles collected should be minimized. Also the number of measurement points within the cycle can be adjusted to provide the desired level of accuracy while maintaining a rapid analysis time.

Controller 118 in step P1010 compares the calculated value to a standard curve. The peak to peak value is performed by rank ordering the magnitude of the normalized summed intensity signals from maximum to minimum and subtracting the minimum value from the maximum value. Alternatively, values may be obtained from preselected points or ranges of values in the rotational cycle and subtracting one value from the other. The AC signal is measured by an analog or digital method and the measured value is always proportional to the peak to peak value, the factor of proportionality being dependent on the method used. A digital method provides point by point data where an analog method provides data analyzed and reported according to a pre-selected data reduction algorithm. Accordingly, it is preferred that there be an unique association between the normalized peak to peak intensity value in the Y-axis and a film thickness on the X-axis. This association is typically performed through a second or third order least squares fit of empirical data that is obtained from samples having known thicknesses, but it may also be performed through other methods known to those skilled in the art.

Controller 118 concludes the test measurement process in step P1012 by interpreting the film thickness measurement in step P1010 to provide an output representing the film thickness or an assay result. For example, in a semiconductor manufacturing process where the film must have a certain specified thickness or it will cause a short circuit in the device that is being manufactured, the output can be a signal that says "pass" if the thickness meets or exceeds the specified value. The output would say "fail" if the thickness falls below the specified value. In thin film binding assays interpretation, increasing thicknesses are interpreted as positive outputs, but a threshold thickness change may also be set below which the results are reported as negative. Results may be reported either qualitatively or quantitatively.

Figure 7:
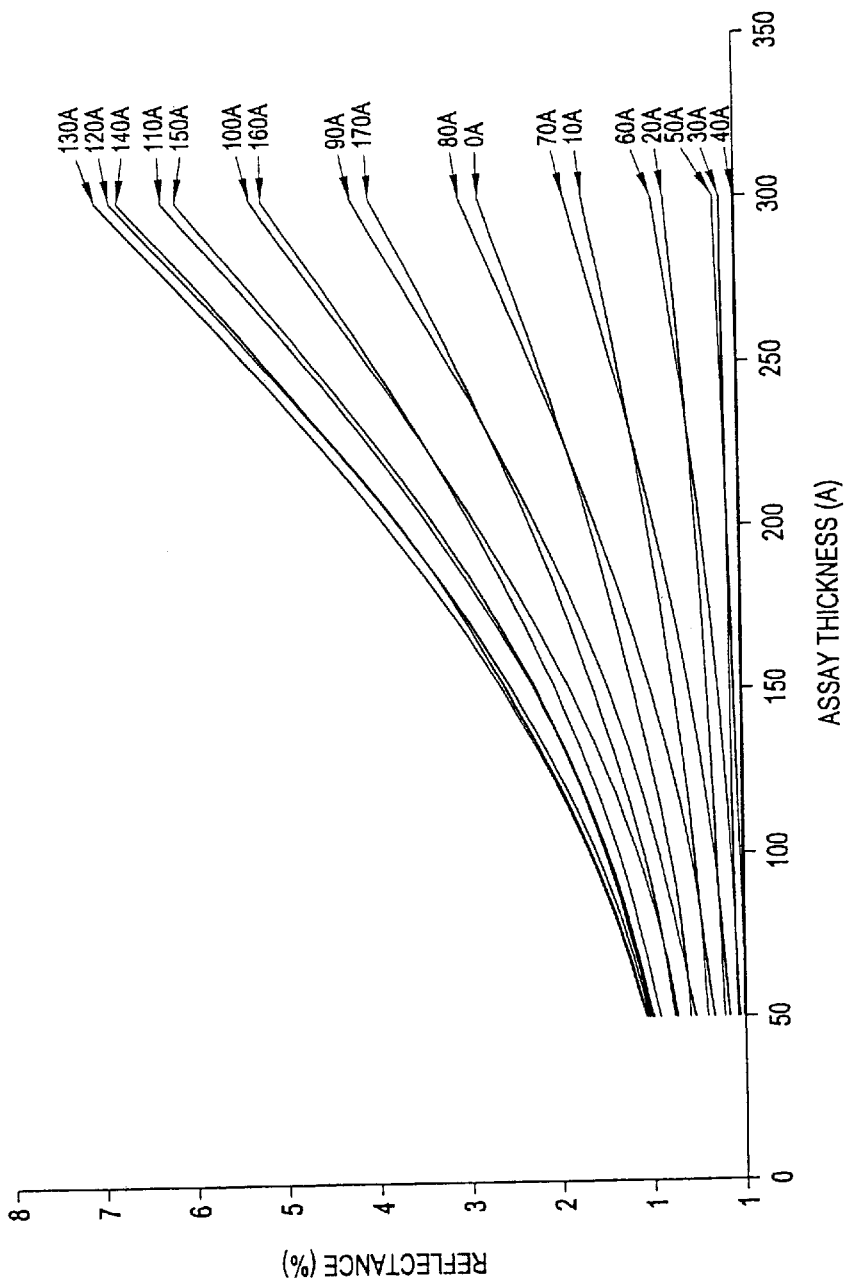
FIG. 7 depicts a modeled AC mode assay system where the results are an increase in intensity as a function of increasing thickness at different analyzer angles.
Figure 10A:
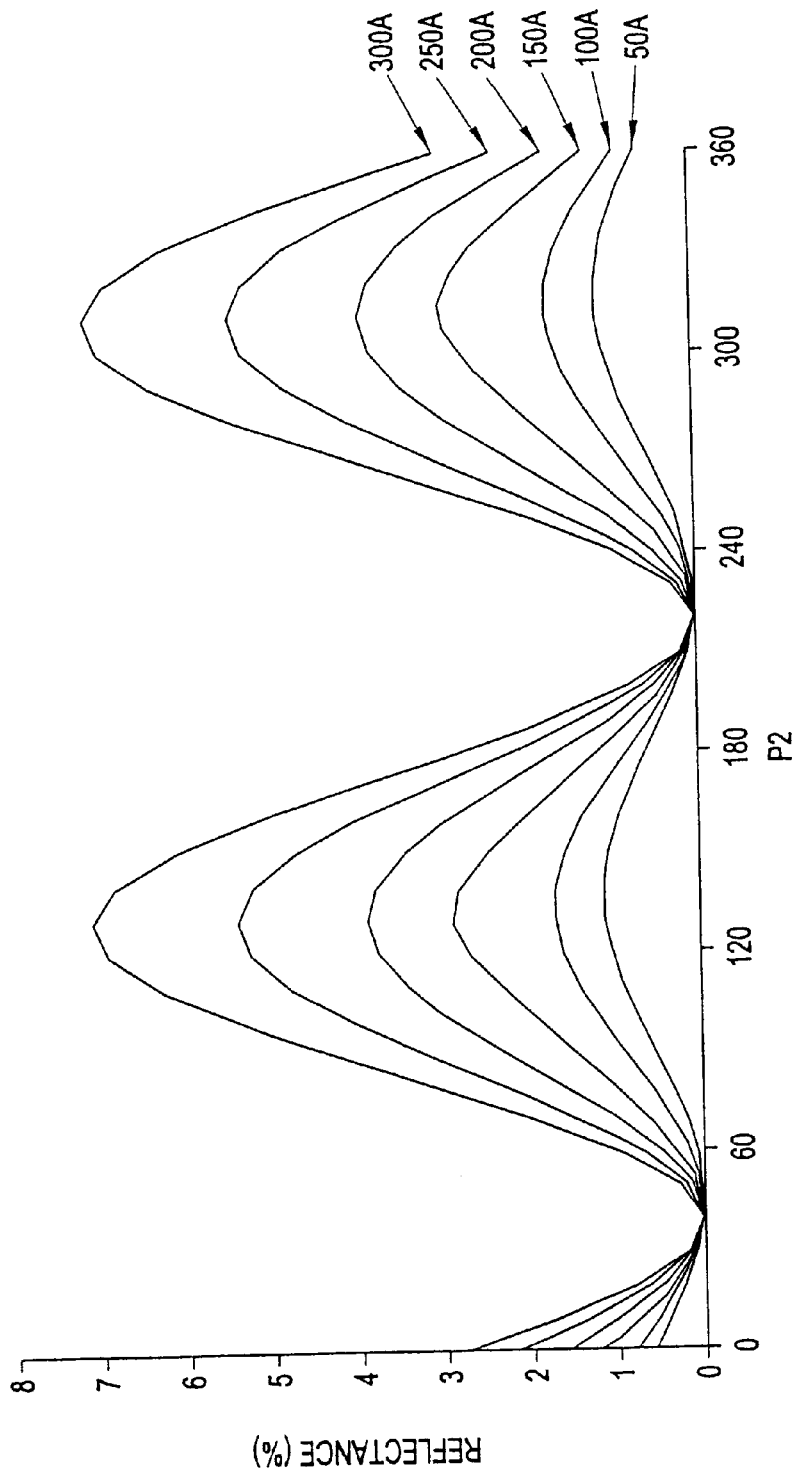
FIG. 10a depicts the theoretical raw quasi-sinusoidal data for the AC mode assay system of FIG. 7 as the analyzing polarizer rotates for varying thicknesses of a binding assay layer above the t-polymer layer.
Figure 10B:
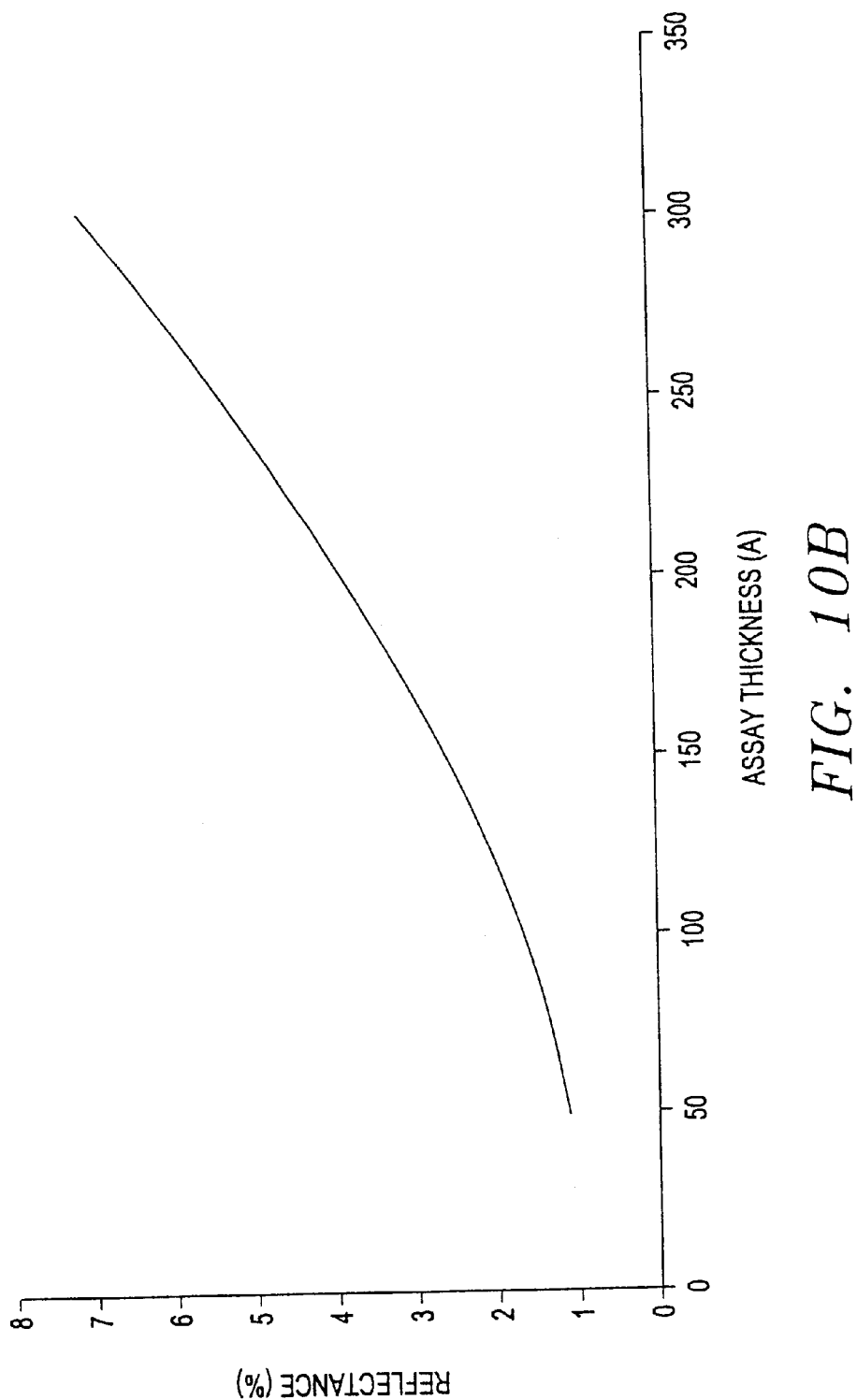
FIG. 10b depicts the theoretical final output for the AC mode assay system of FIG. 7.

FIG. 7 depicts a simulation of an AC mode fixed polarizer ellipsometer for a specific binding assay, surface construction. The optical support used is a monocrystalline silicon wafer that is coated with a 20 Å silicon dioxide layer. The wafer also supports a 475 Å silicon nitride layer and an attachment layer of t-polymer siloxane of 400 Å. The wavelength of the incident light is 525 nm and the angle of incidence is 20° relative to normal and the first polarizing element is fixed at 50°. The plot shows a change in detected intensity as a function of the assay thickness made at various angles for the analyzing polarizer. All the curves demonstrate a positive slope. In the actual instrument design the exact angle of the analyzing polarizer need not be known. The curves shown are the direct mode detection response that would be observed with the fixed polarizer ellipsometer. The AC mode response for this assay construction is shown in FIG. 10a. In FIG. 10a the intensity measured at the detector is plotted versus the changing angle of the analyzer and the quasi-sinusoidal curves are the detector response as a function of a change in the binding assay thickness. The curves in FIG. 10a could also be presented as function of assay time as the analyzer is rotated at a constant speed and the angle of the rotating polarizer need not be known. The instrument does not need to determine the complete polarization state of the light measured by the detector to provide a valid relative measure of the binding assay thickness change. FIG. 10b is the actual peak to peak values plotted versus a change in binding assay thickness and represents the actual instrument output.

Figure 8:
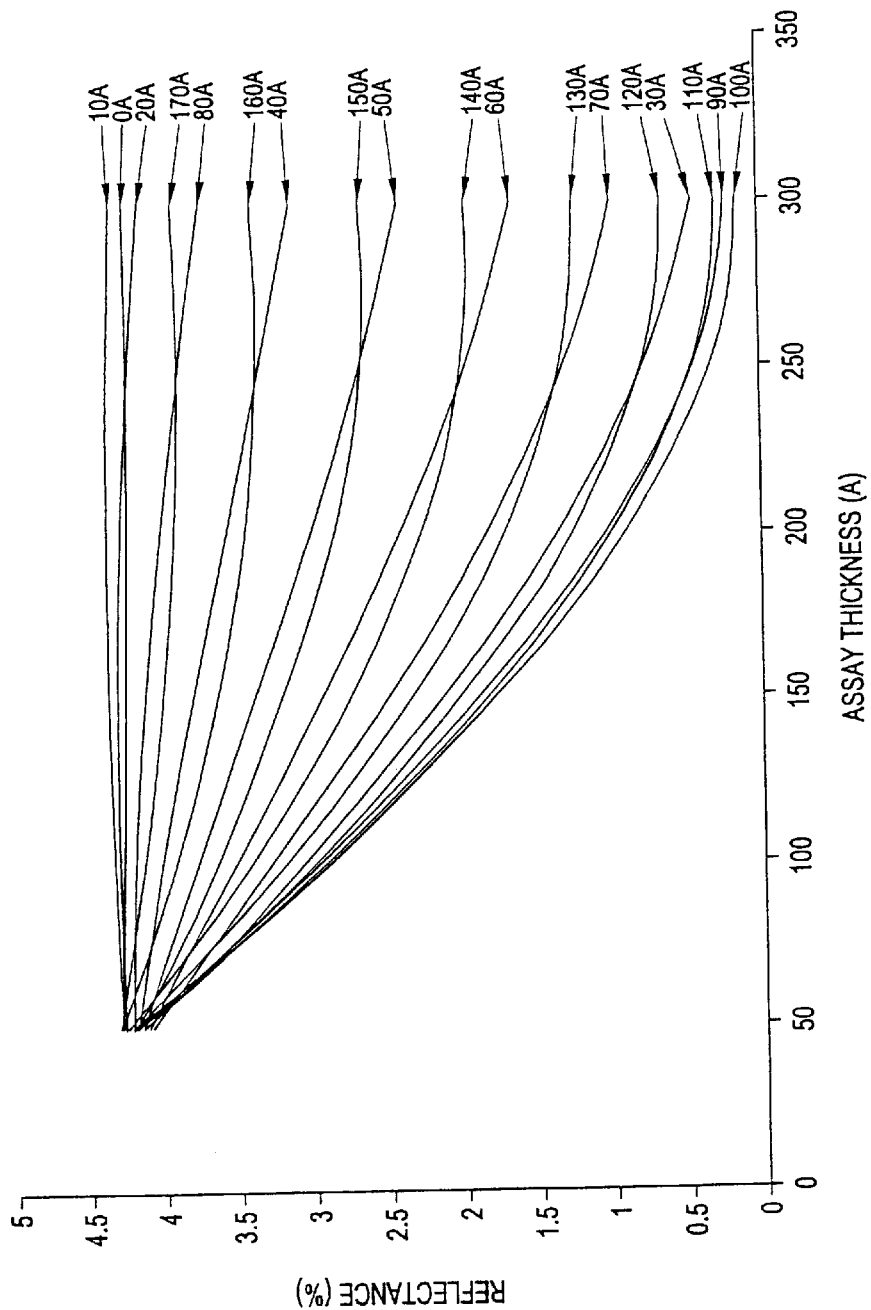
FIG. 8 depicts a modeled AC mode assay system where the results are a decrease in intensity as a function of increasing thickness at different analyzer angles.
Figure 9A:
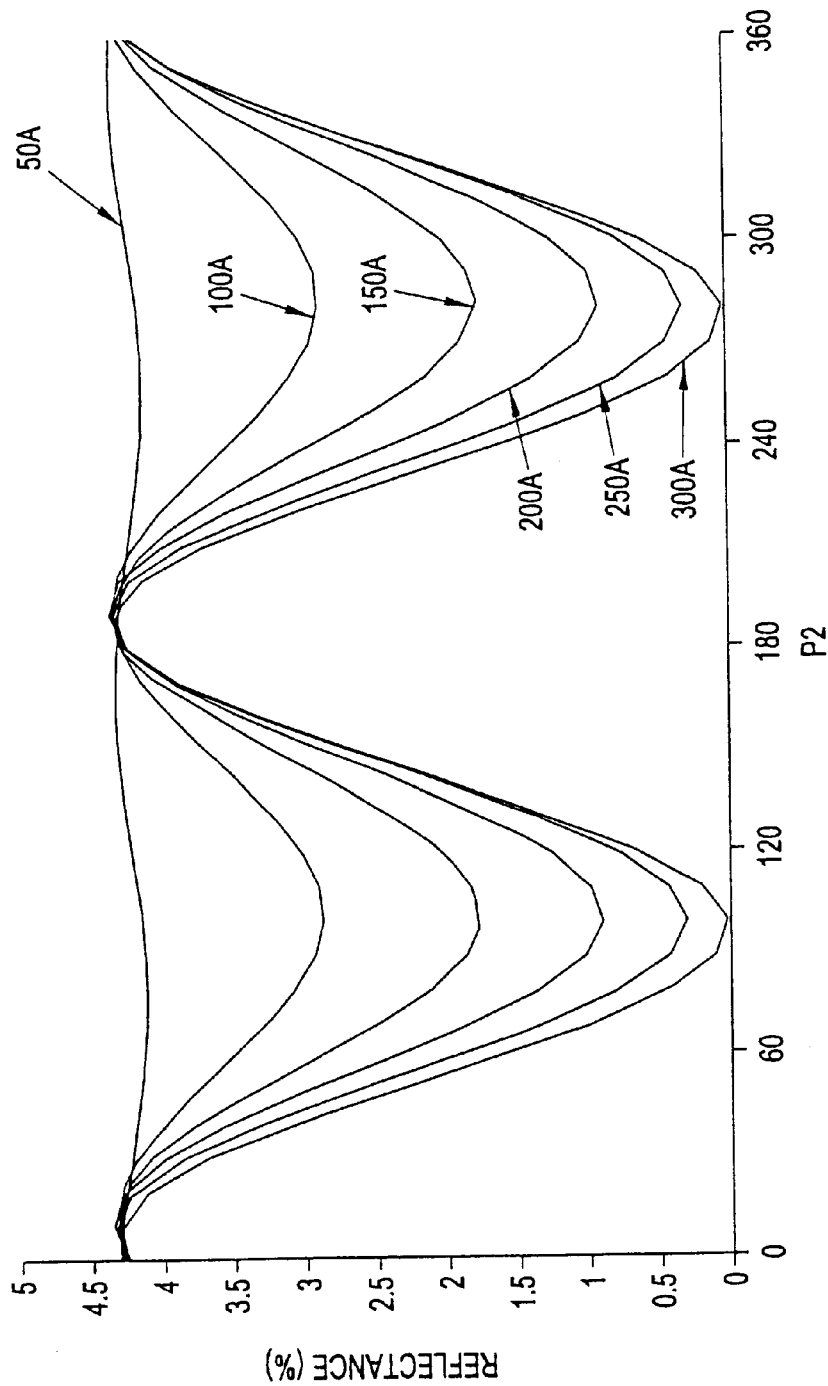
FIG. 9a depicts the theoretical raw quasi-sinusoidal data for the AC mode assay system of FIG. 8 as the analyzing polarizer rotates for varying thicknesses of a binding assay layer above the t-polymer layer.
Figure 9B:
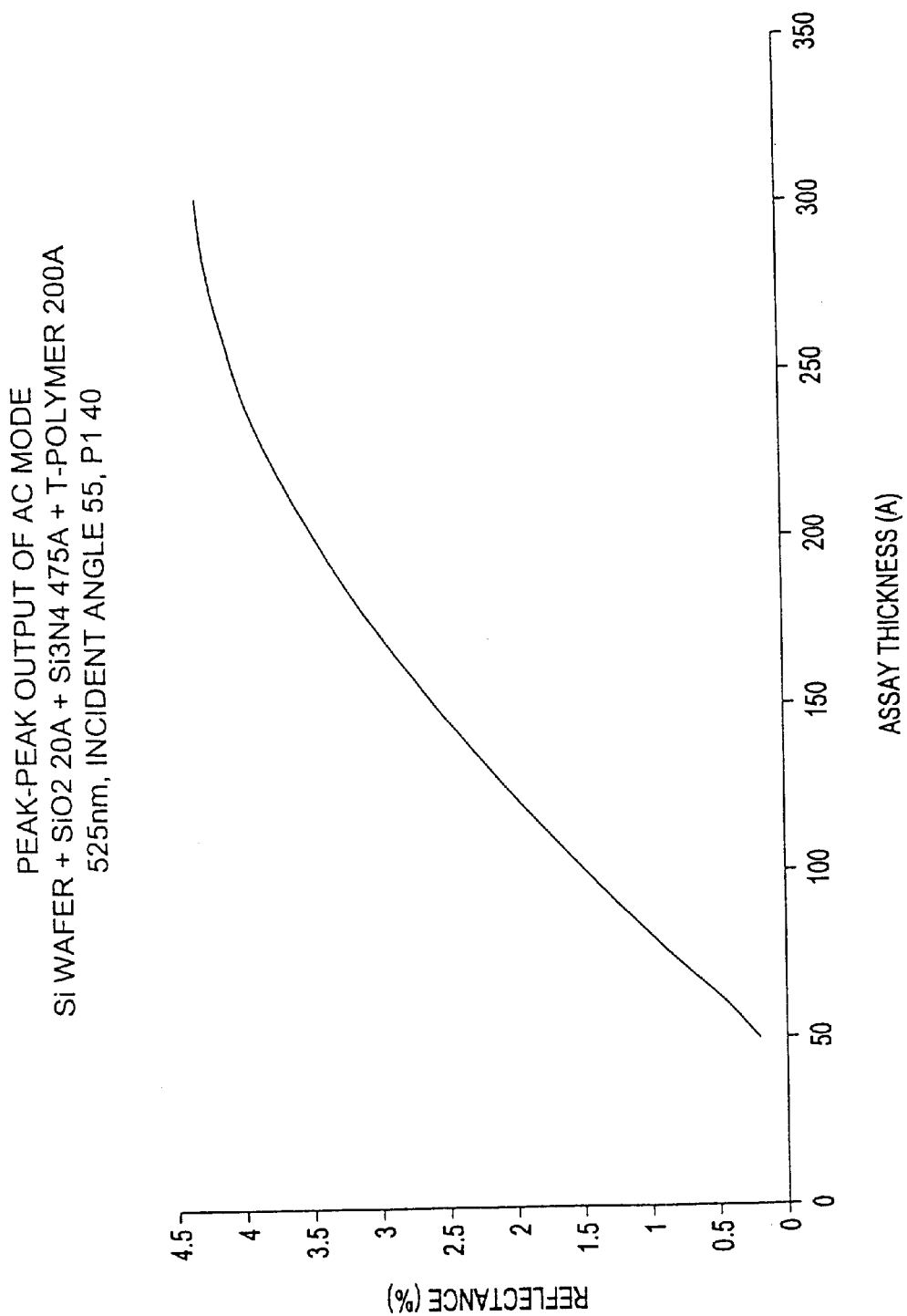
FIG. 9b depicts the theoretical final output for the AC mode assay system of FIG. 8.

FIG. 8 depicts a simulation of an AC mode fixed polarizer ellipsometer for a specific binding assay, surface construction. The optical support used is a monocrystalline silicon wafer that is coated with a 20 Å silicon dioxide layer. The wafer also supports a 475 Å silicon nitride layer and an attachment layer of t-polymer siloxane of 200 Å. The wavelength of the incident light is 525 nm and the angle of incidence is 55° relative to normal and the first polarizing element is fixed at 40°. The plot shows a change in detected intensity as a function of the assay thickness made at various angles for the analyzing polarizer. All the curves demonstrate a negative slope. Again, in the actual instrument design the exact angle of the analyzing polarizer need not be known. The curves shown are the direct mode detection response that would be observed with the fixed polarizer ellipsometer. The AC mode response for this assay construction is shown in FIG. 9a. In FIG. 9a the intensity measured at the detector is plotted versus the changing angle of the analyzer and the quasi-sinusoidal curves are the detector response as a function of a change in the binding assay thickness. The curves in FIG. 9a could also be presented as function of assay time as the analyzer is rotated at a constant speed and the angle of the rotating polarizer need not be known. The instrument does not need to determine the complete polarization state of the light measured by the detector to provide a valid relative measure of the binding assay thickness change. FIG. 9b is the actual peak to peak values plotted versus a change in binding assay thickness and represents the actual instrument output. While the direct measure of thickness in FIG. 8 indicates a negative slope as do the curves in FIG. 9a, the final instrument output, FIG. 9b, is presented as a positive slope with changing assay thickness as the peak to peak value can always be represented as a positive number.

The direct mode theoretical response plots depicted in FIG. 7 and FIG. 8 are used to select the appropriate wavelength, angle of incidence, fixed polarizer settings for a given assay support construction. The instrument parameters are set when the direct mode response plots show the highest degree of signal resolution as a function of thickness change expected for the binding assay system. FIG. 9a and FIG. 10a depict the actual quasi-sinusoidal data collected by the AC mode instruments under the specific conditions selected. FIG. 9b and FIG. 10b depict the actual instrument output.

Reflectometer Instruments

Figure 3:
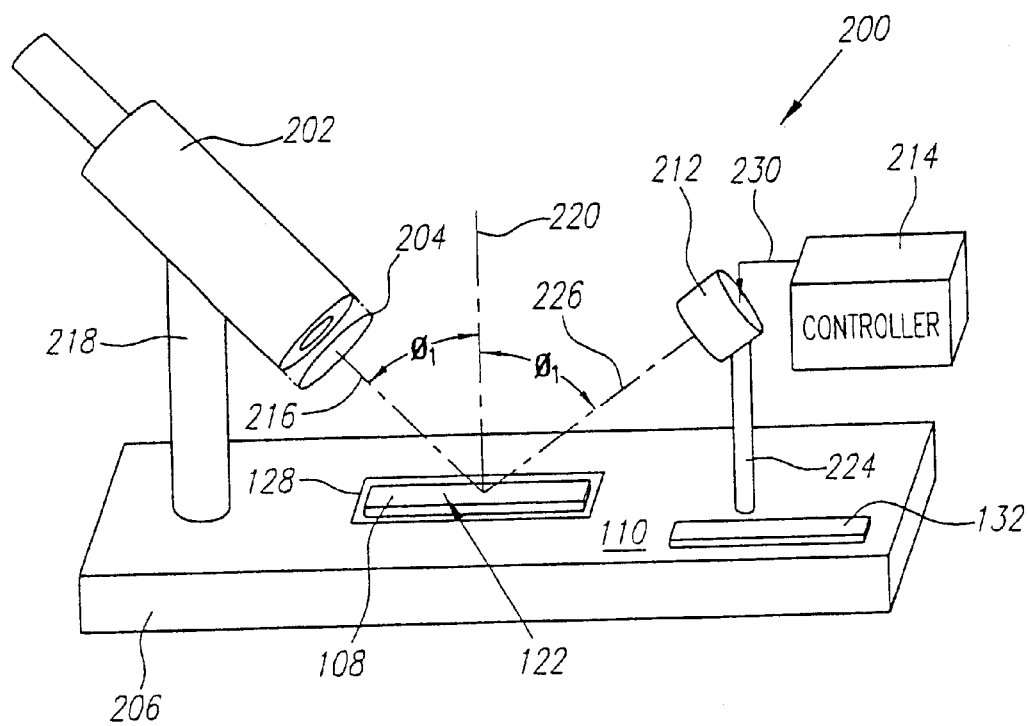
FIG. 3 depicts a thin film-analyzing instrument according to the present invention where the polarizer in the analyzer position is removed.

FIG. 3 depicts a reflectometric thin film instrument 200 according to the present invention. A light source 202 is mounted in fixed relationship with respect to a polarizing filter or polarization element 204 and a support base 206. A film-bearing substrate 108 rests on support surface 110. A detector 212 is positioned to receive reflected light from substrate 108. A controller 214 governs the operation of instrument 200 and receives signals from detector 212.

Light source 202 can be any source of electromagnetic radiation, including a polychromatic or monochromatic light source, but is preferably a monochromatic light source, such as a laser, laser diode, or LED. Light source 202 discharges light along a first or input optical pathway segment 216 to illuminate the film-bearing substrate 108. Light on this first optical pathway segment 216 is polarized by action of the polarization element 204, which is preferably a linear polarizing filter. The polarization element 204 is held in a fixed position and does not move during operation of the instrument 200. During set-up or calibration, polarization element 204 is ideally rotated on its optical axis to provide a pure s- or pure p-polarization content in the polarized light. While a single filter may not be able to provide an absolutely pure s- or p-polarization content, the polarization content is essentially pure. Any undesired component of p- or s-polarization is so small as to be negligible within the design choice specifications of instrument 200.

Mounting base 206 includes a first pillar 218 that selectively retains light source 202 to transmit light in a manner such that first optical pathway segment 216 is at an angle $\phi_1$ representing a departure from a normal line 220. The normal line 220 is taken with respect to a planar surface 122 on substrate 108. The first optical pathway segment 216 can include a narrow beam of light or a wider body of collimated light. In either case, the first optical pathway segment 216 exists at the center of the beam. Selective adjustments may be made by a pair of perpendicular set screws, a ball-pivot friction clamp or any other conventional selective adjustment mechanism (none depicted in FIG. 3). A second pillar 224 provides a similar adjustment mechanism (not depicted in FIG. 3) to align the detector 212 along the reflectance pathway segment 226. This pathway segment 226 departs from vertical by an angle $\phi_1$. An indicia may be formed on surface 110 for positional alignment of substrate 108 with respect to the optical pathway segments defined by 216 and 226 (not shown).

The detector 212 is selected to detect light in wavelengths corresponding to the light that is emitted by light source 202 and reflected by film-bearing surface 108. The detector provides signals that represent the intensity of light at the detector. Detector 212 transmits these signals to controller 214 on cable 230, and controller 214 interprets these signals by associating them with a relative film thickness.

A control sample 132, i.e., a substrate having no thin film or a negative control sample, rests on surface 110. Sample 132 may be substituted for substrate 108 to obtain a background detector signal or unreacted segments of 108 or negative control zones of 108 may be used.

According to the principles of multilayer reflection, the signal intensity at the detector is a direct indicator of film thickness, but a direct computation of this value is complicated or made impossible by the related mathematics and the need to acquire indices of refraction for each of the layers.

The reflectometric thin film instrument 200 is typically used to associate a film thickness with a signal intensity from the detector 212. For example, the presence or absence of a film is interpreted as an increase or decrease in a signal relative to a background signal corresponding to the negative control sample 132. The presence or absence of a film is interpreted as a positive or negative result in a thin film binding assay. The exact selection of delimiting values depends upon the specific application in the intended environment of use, and is a matter of design choice in programming controller 214.

Figure 4:
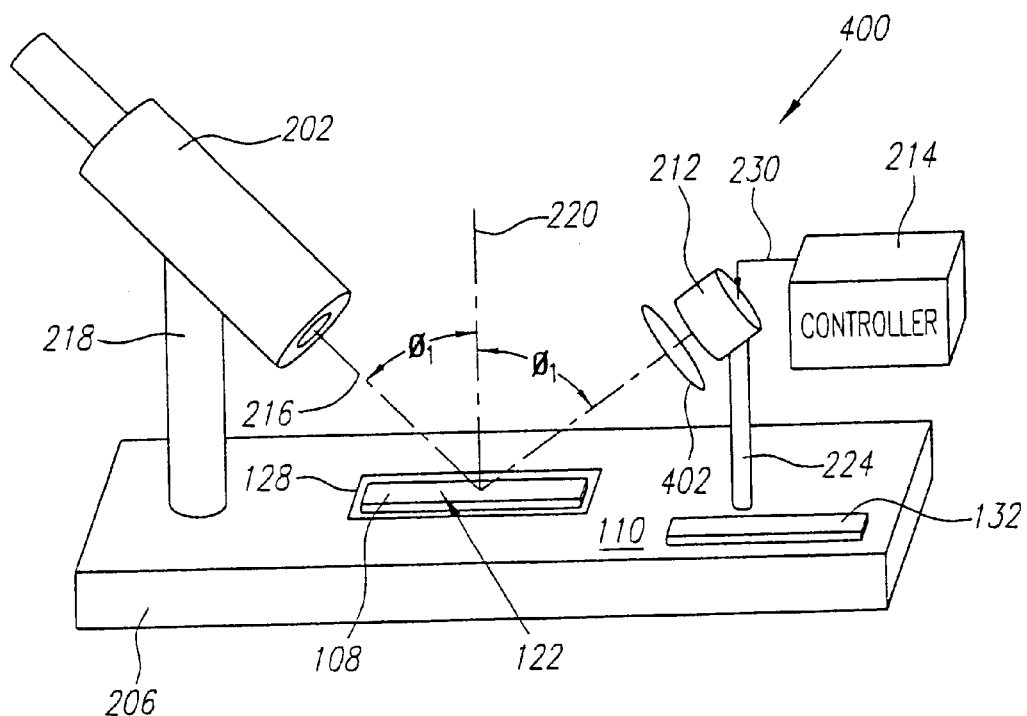
FIG. 4 depicts a thin film-analyzing instrument according to the present invention where the polarizer in the polarizer position is removed.

FIG. 4 depicts a second thin film instrument 400 according to the present invention. All of the components common to instrument 200 and instrument 400 are numbered with the same identifier. Instrument 400 differs from instrument 200 in that the polarization element 204, which exists between light source 202 and the substrate 108 (or support surface 110) in instrument 200, is absent from instrument 400. In instrument 400, the polarization element 204 of instrument 200 has been replaced by the addition of polarizer 402 at a position between the substrate 108 and detector 212. The operation of instrument 400 is identical to that of instrument 200 because polarizer 402 is rotated on its optical axis to allow passage of an essentially pure s- or p-polarization component and then fixed in that position. Thus, in either instrument 200 or instrument 400, only the attenuated polarization component is allowed to pass through to the detector.

The instruments 200 or 400 are configured in terms of wavelength of incident light, s- or p-polarization state, and angle of incidence that are selected based on empirical or theoretical determinations. The selected configuration is designed to address a specific combination of optical substrate and a range of thicknesses of the thin films to be deposited on the substrate. The range of thicknesses considered in the theoretical calculations must include any layers above the substrate used to create or improve reflectivity, improve or create a favorable environment for attachment of biological materials, the receptive layer, the analyte layer, and the amplification reagents where required.

Figure 11:
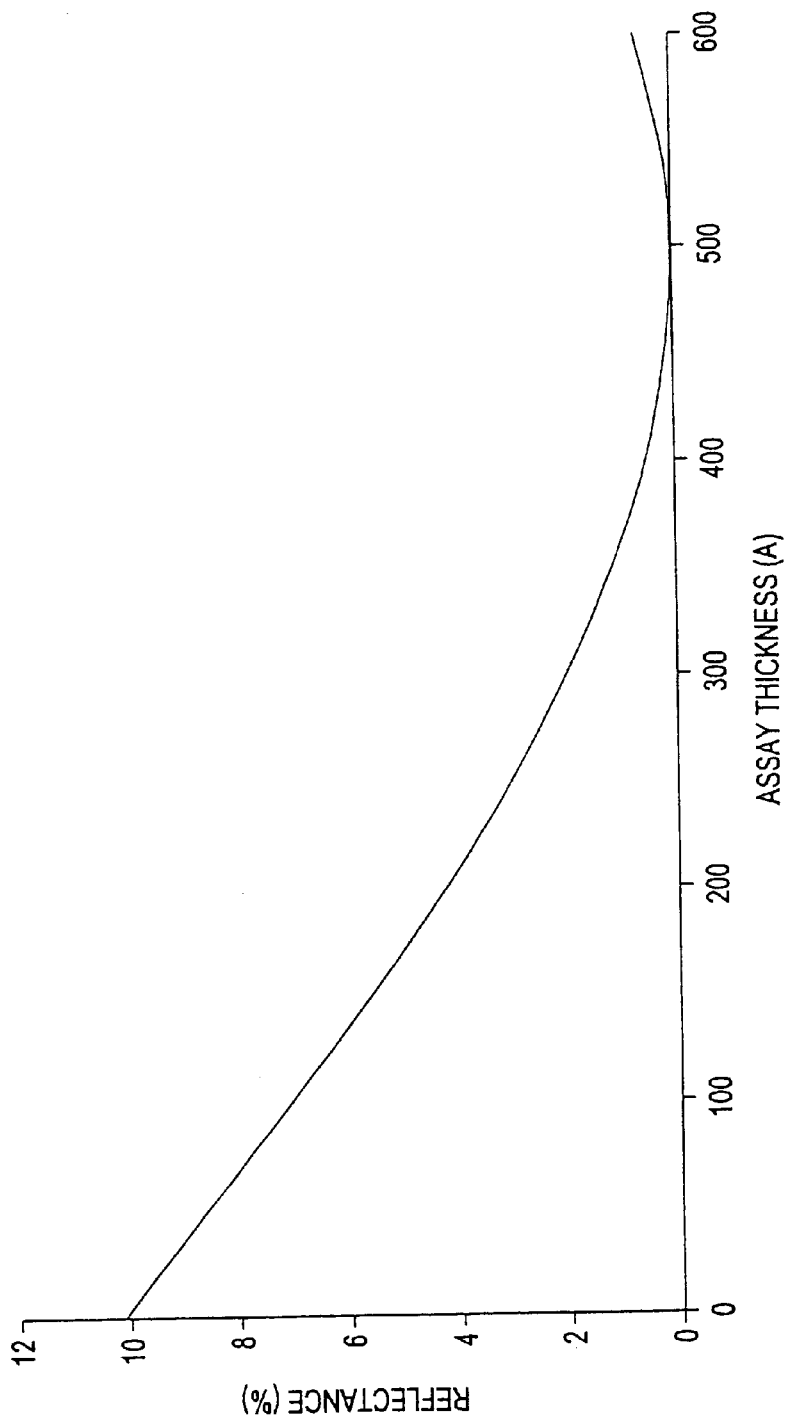
FIG. 11 depicts a theoretical output for a single polarizer instrument in combination with a specific surface construction.

FIG. 11 depicts a theoretical instrument response curve for a single fixed polarizer reflectometer where the assay surface construction includes a silicon wafer as the optical support. The wafer supports a 20 Å silicon dioxide layer, a 475 Å layer, and a 100 Å diamond like carbon (DLC) layer for optical and attachment purposes. The instrument utilizes a 635 nm incident light source with a 35° angle of incidence relative to the normal. The polarizing element is placed on the incident side of the instrument and is set at a 90° angle to deliver s-polarized light to the surface. Under these conditions the response curve has a negative slope as a function of increasing binding assay thickness. If the binding assay produces greater than a 500 Å change in thickness this instrument configuration will not be appropriate as a minimum response is maintained from approximately 480 to 520 Å.

Polarizer-free Reflectometric Instruments

Figure 5:
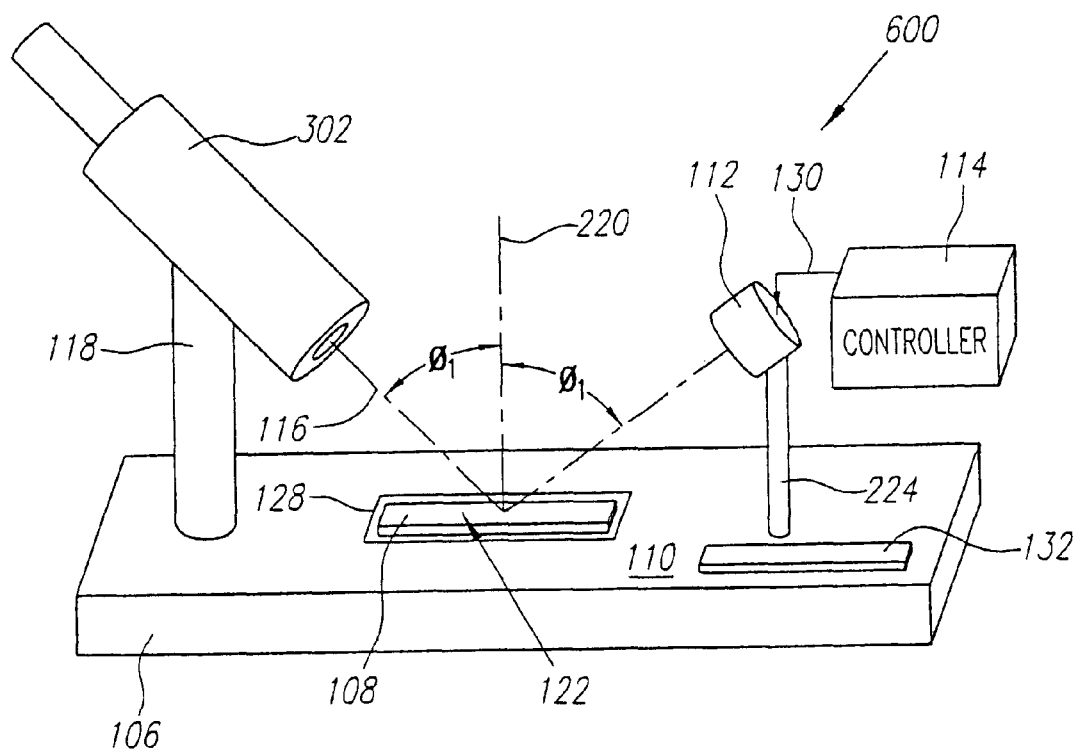
FIG. 5 depicts a thin film-analyzing instrument according to the present invention where all polarizing elements have been removed.

FIG. 5 depicts a third reflectometric embodiment of the invention, namely, thin film instrument 600. Components common to instrument 200 and 400 carry the same identifier as in previous figures. Instrument 600 differs from instrument 200 in that the polarization element 204, which exists between light source 202 and the substrate 108 (or support surface 110) in instrument 200, is absent from instrument 600. In instrument 600, the polarization element 204 of instrument 200 has not been replaced by any other polarizing filter. In addition the polarizer 402 found in instrument 400 has been removed.

Instrument 600 operates on the principle that the p-amplitude reflection coefficients are theoretically equal to the s-amplitude reflection coefficients when the angles of incidence and reflectance are at normal. In non-theoretical devices, these angles can approximate zero but cannot be exactly zero because the light source and the detector would have to occupy the same space. The receipt of un-polarized light at the detector is a special case that does not require multiple polarizing filters to resolve ellipticity in calculating film thicknesses. Since at $\phi_1=0$ (or very low angles from the normal), $r_s=r_p$, it makes no difference how much light is in the s- or p-state, so any polarization state is acceptable. As a practical matter, the angle $\phi_1$ can range from 0° to 30° without introducing a sufficient imbalance of the reflectance of s- and p-polarized components that would introduce thickness measurement errors arising from the ellipticity of s- and p-polarized light. This range is more preferably from 0° to 20° and is most preferably from 0° to 10° or smaller.

Figure 12:
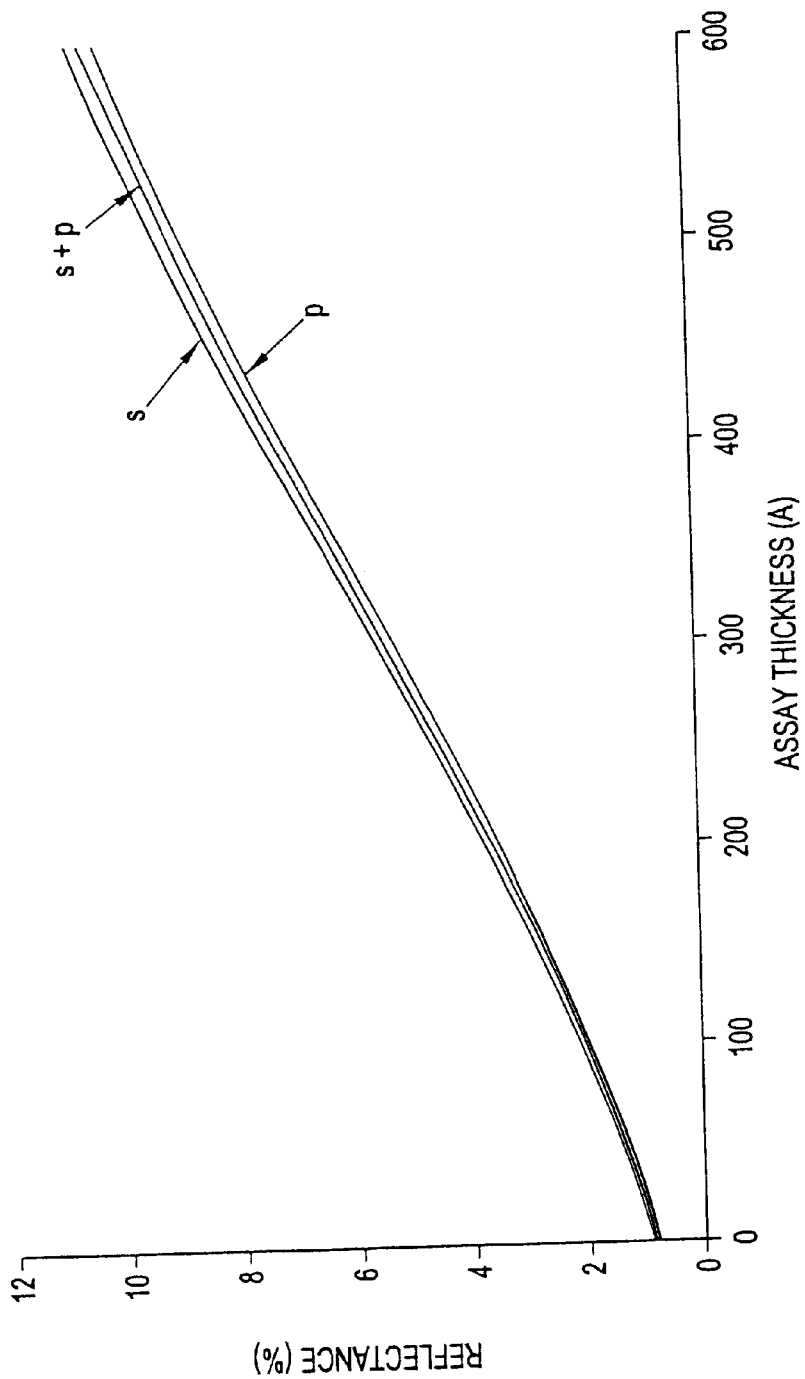
FIG. 12 depicts a theoretical output for an instrument with no polarizing elements as a function of the polarization state of the incident light and at very small angles of incidence.

FIG. 12 depicts theoretical response curves for a reflectometric instrument with no polarizing elements and a small angle of incident light (10°) relative to the normal. In this case the instrument is constructed to analyze a silicon wafer with a 20 Å silicon dioxide layer and a 475 Å silicon nitride layer. An additional layer of 300 Å DLC is included in the assay support construction. The incident light source provides a 635 nm wavelength. The theoretical analysis compares the intensity change as a function of binding assay thickness for a light source that provides either a p-polarization state only, an s-polarization state only, or is unpolarized. Surprisingly, under these conditions the unpolarized light is essentially comparable to either polarized light sources. Thus, a reflectometer based on an unpolarized light source in an instrument with no polarizing elements at a small angle of incidence should provide good thickness resolution for a binding assay based on the modeled assay surface construction.

Thin Film Measurements in Bioassay Interpretation

All of the thin film-analyzing instruments of this invention are especially useful in providing thin film measurements that are highly specific and highly sensitive indicators of bioassay results and, particularly, binding assays such as immunoassays or nucleic acid hybridization assays. In binding assays a solid support is coated with a material that is specific to an analyte of interest. An analyte is any material that is uniquely associated with a specific desired disease, condition, environment, etc. Sandstrom et al., U.S. Pat. No. 5,494,829, describes numerous thin film binding assay techniques, and is hereby incorporated by reference to the same extent as though fully disclosed herein. The most preferred binding assays involve the use of enzyme/substrate pairs that produce an insoluble precipitated reaction product. The catalytic nature of this reaction amplifies the sensitivity of the assay by continuously precipitating a reaction product to build a film thickness. The enzyme is introduced into the thin film binding assay through conjugation of the enzyme to an analyte specific reagent.

More generally, any reaction process that provides a specific component that can be attached to a receptive material through interaction with a specific analyte and can catalyze conversion of a substrate to a precipitated film reaction product is suitable for this type of catalytically amplified binding assay. Enzymes that are useful for this amplification purpose include glucose oxidase, galactosidase peroxidase, alkaline phosphatase, and the like.

Figure 6:
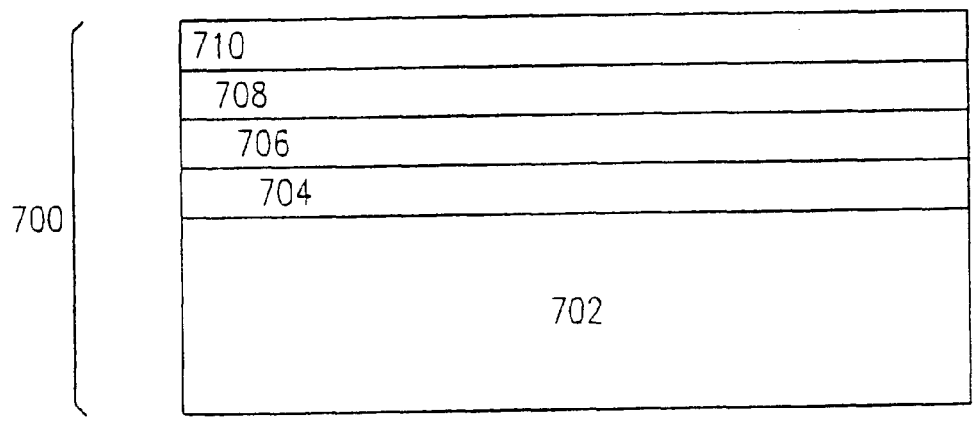
FIG. 6 depicts an assay surface construction suitable for analysis with any of the thin film-analyzing instruments of the invention.

FIG. 6 depicts a sample 700 for use in binding assays. The sample 700 corresponds to substrate 108 of FIG. 1 and is used as a sample for analysis in thin film measurements after it has been incubated with a specimen that is taken from a patient who may be infected with a particular microorganism or combination of microorganisms or another source of test material. The respective layers of sample 700 are not drawn to any relative scale, and have been drawn for purposes of discussing concepts that pertain to the use of thin film analyzing instruments in the interpretation of binding assays. An optical support 702 provides the primary structural support for all other layers. This optical support may be a conventional polished silicon wafer, and is preferably monocrystalline silicon, though alumina, glass, and other types of reflective materials may also be used. The optical support may support any number of additional films. The primary consideration for selection of optical support 702 is the reflectivity of the material and or its ability to be coated with a reflective material. The optical support must be compatible with the coating processes used to create subsequent layers and must be stable to the testing environment.

An optional film, 704, may be used to create an adjustment layer. By selecting a proper thickness of this, as well as the wavelength of light and the angle of incidence used in the instrument, the thickness-reflectance curve can be optimized to give the maximum thickness sensitivity. An anti-reflective film attenuates one or more wavelengths of light through the destructive interference of that wavelength at the various interfaces of the thin film structure 700. An attachment layer 706 functions to improve the adhesion of analyte specific binding reagent to the surface of the optical support 702 or the optical film 704 when it is present. Certain films may perform both the optical function and the attachment function. The suitability of a single film for both functions should be tested in conjunction with the analyte specific binding reagent to ensure that an adequate density of reagent can be achieved and retained on the surface. The analyte specific binding layer is 708. Representative analyte specific binding reagents include antibodies, antigens, nucleic acids, receptors, chelators, etc. A protective layer is optionally used to protect the bioreceptive layer 708 during storage (layer not indicated). This protective layer dissolves during incubation with an analyte solution.

During the binding assay the analyte specific layer reacts with analyte to create layer 710. Layer 710 also consists of the amplifying reagent such as an antibody conjugated to an enzyme. The layer also consists of the precipitated or bound reaction product that is produced by interaction the enzyme with an appropriate enzyme substrate. The amplifying material could also be non-enzymatically generated.

It is an especially preferred feature of the invention that the attachment layer 706, the analyte specific binding layer 708, and the analyte containing and precipitated reaction product layer 710 have approximately the same indices of refraction. Thus, based on that assumption, these layers are assumed to function as one layer, and the device is easily calibrated by the results of theoretical calculations. On the other hand, while the mathematical solution is much more complex where these indices or refraction are significantly different, the principles of operation that result in the quasi-sinusoidal curves at the detector remain the same.

The optional optical layer 704 is preferably formed of materials such as titanium dioxide or silicon nitride. And these materials may be sputter-deposited under vacuum or spun-on from metal alkoxide and metal carboxylate precursor liquids, which are pyrolized in oxygen or nitrogen ambients to produce the desired film. For example, an organotitanate known as Tyzor TPT (tetraisopropyltitanate) may be purchased from Dupont. One ml of the organotitanate solution may be mixed with 3 ml of glacial acetic acid, 3 ml of alcohol, 3 ml deionized water, and 10 $\mu$l of 3M's FC171 fluorosurfactant. Isopropanol, t-amyl alcohol, ethanol, or acetone may be used with the water for this application. Ethanol should be used sparingly or avoided because it leads to precipitation of the titanium. About 500 $\mu$l of this mixture is applied to a wafer to produce a uniform film by a static spin-coating technique. The film is cured by heating in an oven to 250° C. for two hours or by microwaving the wet-coated wafer at 400 watts for two minutes.

There are several suitable binding agents for use in attachment layer 706. These include (trimethoxysilylpropyl) polyethyleneimine (e.g., PEI from Petrarch of Bristol, Pa.), which is typically diluted 1:500 in methanol, spun or sprayed onto a wafer, and cured at 100° C. under a vacuum of 0.1 mmHg to provide a thickness of about 80 Å. The binding agent may be improved to form branch points along the linear PEI chain by exposing the PEI film to dimethyldichlorosilane (e.g., DMDCS from Sigma Chemical Co. of St. Louis, Mo.), which is typically mixed to a concentration of about 2% by volume in 1,1,1-trichloroethane. Submersion of the PEI-coated wafer in this solution for 60 minutes at 25° C. followed by an alcohol rinse and drying under nitrogen flow yields an attachment layer about 200 Å thick. Polystyrene (e.g., commercially available polystyrene from Becton Dickinson of Oxnard, Calif.) may be dissolved in toluene or another solvent to a ratio of 0.025 g/ml, spun-on to a wafer, and cured for 60 minutes are 25° C. to yield a final layer about 200 Å thick. The MSA-Starburst polymers from Polysciences of Warrington, Pa. may be diluted 1:4 (v/v) in methanol, spun-on to the wafer, and cured for 120 minutes by baking at 25° C. in air to yield a final attachment layer about 40 Å thick. Other suitable binding agent materials include the TC7A film-forming latex material from Seradyn of Indianapolis, Ind.; Dimethyldiphenyl siloxane copolymer (e.g., DMDPS from Petrarch of Bristol, Pa.); mercaptopropylmethyldimethyl-siloxane copolymer (e.g. mercapto from Petrarch of Bristol, Pa.); N-(2-aminoethyl-3-aminopropyl)trimethoxysilane (e.g., BAS Petrarch of Bristol, Pa.); triethoxysilyl modified polybutadiene (e.g., PBD from Petrarch of Bristol, Pa.); and (methylphenyl) methyldodecyl-methylaminopropyl-methyl-siloxane. These materials are used to bind bioreceptive layer 706 according to conventional methods.

The analyte specific binding layer 708 includes a receptive material that is defined as one part of a specific binding pair. This includes, but is not limited to: antigen/antibody, enzyme/substrate, oligonucleotide/DNA, chelator/metal, enzyme/inhibitor, bacteria/receptor, virus/receptor, hormone/receptor, DNA/RNA, oligonucleotide/RNA, and binding of these species to any other species, as well as the interaction of these species with inorganic species. For example, subclasses of analyte specific binding materials include toxins, antibodies, antigens, hormone receptors, parasites, cells, haptens, metabolites, allergens, nucleic acids, nuclear materials, autoantibodies, blood proteins, cellular debris, enzymes, tissue proteins, enzyme substrates, co-enzymes, neuron transmitters, viruses, viral particles, microorganisms, polysaccharides, chelators, drugs, and any other member of a specific binding pair.

The receptor material is characterized by an ability to specifically bind the analyte or analytes of interest. The analyte or analytes of interest are obtained from a test specimen to be analyzed for a specific state or condition such as a disease. The specimens may be found in the matrix of such materials as fluids, solids, or gasses; especially mucous, saliva, urine, feces, tissue, marrow, cerebral spinal fluid, serum, plasma, whole blood, sputum, buffered solutions, extracted solutions, semen, vaginal secretions, pericardial, gastric, peritoneal, pleural, or other washes, and the like. Or the specimen may be a soil or water sample or a food sample, etc. The presence of an analyte is an indicator of infectious disease, cancer, metabolic disorder, food poisoning, toxic exposure, drug abuse, or levels of therapeutic agents. The presence of an analyte may also indicate environmental pollution, presence of an undesired waste product, food contamination, etc.

The amplifying reagent that is one component of layer 710 is most preferably an enzyme-labeled antibody. For example, an insoluble reaction product results when an immobilized antibody-antigen-antibody-enzyme complex is present on the test surface. A reaction product is catalytically precipitated by the action of the enzyme on a precipitating agent in solution. Precipitating agents include combinations of alginic acid, dextran sulfate, methyl vinyl ether/maleic anhydride copolymer, or carrageenan and the like, as well as the product formed by the interaction of TMB (3,3',5,5'-tetra-methyl-benzidine) with an oxygen free radical. This particular precipitating agent forms an insoluble product whenever a free radical contacts the TMB. Other substances including chloronapthol, diaminobenzidene tetrahydrochloride, aminoethyl-carbazole, orthophenylene-diameine and the like can also be used as precipitating agents. The precipitating agent is typically used in concentrations ranging from about 10 mM to 100 mM. But any material that can be attached to an analyte specific binding reagent and can serve to increase the thickness of layer 710 can be utilized.

EXAMPLES

Example 1

Enzyme Amplification of Binding Assay

Horseradish peroxidase (Sigma grade VI) was chemically coupled to immunoglobulins that were purified by caprylic acid precipitation from pooled high titer sera from rabbits that were previously injected with suspensions of cells form cultures of *Neisseria meningitidis* A, C, Y, $W_{135}$. The coupling was done using the reagent S-acetyl thioacetic acid N-hydroxysuccinimide ester according to conventional methods that are described in *Analytical Biochemistry* 132 (1983) 68–73. The resultant conjugate contained peroxidase (104 $\mu$M) and immunoglobulin (35 $\mu$M) in a buffer of 4-morpholinepropanesulfonic acid (MOPS), 50 mM, pH 7.0. The peroxidase-immunoglobulin conjugate was diluted in MOPS buffer together with casein (5 mg/ml) and mixed with an equal volume of a dilution of a cell-free filtrate from a culture of *Neisseria meningitidis* organisms.

A 25 $\mu$l aliquot of the mixture was transferred by pipette to the surface of a silicon wafer coated with layers of silicon nitride, T-polymer siloxane, and purified immunoglobulin from the same rabbit antibody preparation to *Neisseria meningitidis*. Antibody was coated to the t-polymer/silicon wafer from a solution containing 10 μg/ml of antibody in 50 mM MOPS, pH 7.0. The wafer remained submersed in the antibody for 1 hour at ambient temperature, was rinsed with deionized water, and dried under a stream of nitrogen. The antibody coated substrate was further treated by incubating the coated substrate in 0.5 mg/ml hydrolyzed casein in 50 mM MOPS pH=7.0 for 1 hour at ambient temperature followed by rinsing and drying.

The conjugate solution containing peroxidase, immunoglobulin, and cell-free filtrate from *Neisseria meningitidis* organisms was applied to the surface of the wafer and permitted to incubate to 2 minutes. The sample was washed with water and dried under a stream of nitrogen. Blotting with a filter device is also suitable for drying purposes. A solution of a precipitating TMB substrate was applied to the surface for 4 minutes and then washed and dried as before. The wafer containing the precipitated reaction product is placed in thin film analyzing instruments for thickness determination.

These procedures can, for example, be repeated for *H. influenza* Group B, *Streptococcus pneumoniae,* Streptococcus Group B, and *E. coli* K1.

The specific type of receptive pair interaction is unimportant to the purpose of the invention. Exemplary types of binding assay interactions include binding assays for Human Immunodeficiency Virus, (HIV) I or II or a combination thereof, Streptococcus Group A, Streptococcus Group B, Respiratory Syncitial virus, Hepatitis B, a Chlamydia species, and Herpes Simplex virus.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned; as well as those inherent therein. The cell lines, embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are set forth within the following claims.

I claim:

1. A device for use in determining a film thickness of a sample, the device comprising:
   a substrate for supporting said sample;
   a light source for producing electromagnetic radiation to illuminate said sample;
   a first polarization element located between said light source and said sample;
   a detector for detecting electromagnetic radiation reflected from said sample;
   a second polarization element located between said detector and said sample; and
   a data analysis means for utilizing a signal obtained from said detector to determine film thickness,
   wherein the polarization state of electromagnetic radiation illuminating said sample is not changed by a component of said device between said first polarization element and said sample and the polarization state of electromagnetic radiation reflected from said sample is not changed by a component of said device between said sample and said second polarization element; and
   wherein at least one of said first and second polarization elements is a rotatable element which rotates during an operating mode of said device to vary an s and/or p component of said electromagnetic radiation with time, and wherein said data analysis means uses a standard function that correlates film thickness to detector signal intensity.

2. A device according to claim 1, wherein said light source produces monochromatic electromagnetic radiation.

3. A device according to claim 1, wherein said electromagnetic radiation is selected from the group comprising visible light, infrared light, and ultraviolet light.

4. A device according to claim 1, wherein said first polarization element comprises a rotatable polarizing filter.

5. A device according to claim 1, wherein said second polarization element comprises a rotatable polarizing filter.

6. A device according to claim 1, wherein said first polarization element comprises a rotatable polarizing filter, and wherein said second polarization element comprises a fixed analyzer.

7. A device according to claim 5, wherein said first polarization element comprises a fixed polarizing filter, and wherein said second polarization element comprises a rotatable analyzer.

8. A device according to claim 1, wherein at least one of said first and second polarization elements is rotated to provide a quasi-sinusoidal intensity signal at said detector.

9. A device according to claim 8, wherein said film thickness is related to an amplitude of said quasi-sinusoidal intensity signal.

10. A device according to claim 8, wherein said film thickness is related to a peak to peak amplitude of said quasi-sinusoidal intensity signal.

11. A device according to claim 1, wherein said device further comprises a control sample comprising a known film thickness.

12. A device according to claim 11, wherein the control sample is a negative control sample.

13. A device according to claim 12, wherein the standard function comprises a normalizing function which relates said detector signal intensity to a comparative detector signal intensity obtained from said negative control sample.

14. A device according to claim 13, wherein the normalizing function is a ratio of said detector signal intensity and said comparative detector signal intensity obtained from said negative control sample.

15. A device according to claim 1, wherein said light source is positioned at a prefixed angle relative to the substrate, and said detector is positioned at said prefixed angle relative to the substrate.

16. A method of measuring a film thickness of a sample, the method comprising:
    providing a device comprising a light source, a polarizer, an analyzer, and a detector;
    directing electromagnetic radiation from the light source towards the sample, whereby electromagnetic radiation is reflected from the sample;
    polarizing the electromagnetic radiation that is directed towards the sample using the polarizer, wherein the polarization state of electromagnetic radiation illuminating said sample is not changed by a component of said device between said polarizer and said sample;
    polarizing the electromagnetic radiation reflected from the sample using the analyzer, wherein the polarization state of electromagnetic radiation reflected from said sample is not changed by a component of said device between said sample and said analyzer;
    rotating the polarizer or the analyzer to vary the s and p content of the polarized electromagnetic radiation with time;
    detecting the polarized electromagnetic radiation reflected from the sample using the detector, whereby a signal is obtained corresponding to the intensity of the reflected electromagnetic radiation; and
    correlating the signal to the film thickness of the sample, wherein said correlation step comprises using a standard function that relates film thickness to detector signal intensity.

17. The method of claim 16, wherein said standard function is selected from a plurality of standard functions obtained from samples having different optical properties.

18. The method of claim 16, wherein said method further comprises providing a comparative detector signal intensity obtained from a negative control sample.

19. The method of claim 18 wherein the standard function comprises a normalizing function which relates the detector signal intensity to the comparative detector signal intensity.

20. The method of claim 19, wherein the normalizing function is a ratio of the detector signal intensity and the comparative detector signal intensity.

21. The method of claim 16, wherein rotating the polarizer or the analyzer provides a corresponding quasi-sinusoidal signal from the detector.

22. A device for use in interpreting thin film binding assays, the device comprising:
    a substrate for supporting a sample;
    a light source for producing electromagnetic radiation to illuminate said sample;
    a detector for detecting electromagnetic radiation reflected from said sample,
    wherein a signal produced by said detector corresponds to the intensity of said reflected electromagnetic radiation;
    an optical pathway between said light source, said sample, and said detector, said optical pathway comprising a single polarization element within said optical pathway, wherein said single polarization element is a fixed polarization element located between said light source and said sample to linearly polarize said electromagnetic radiation; and
    a signal processor for interpreting a thin film binding assay by correlating said signal with a film thickness of said sample.

23. A device according to claim 22, wherein said linearly polarized electromagnetic radiation is essentially s-polarized relative to a plane of incidence in said optical pathway between said polarizer and said detector.

24. A device according to claim 22, wherein said linearly polarized electromagnetic radiation is essentially p-polarized relative to a plane of incidence in said optical pathway between said polarizer and said detector.

25. A device according to claim 22, wherein said film thickness is related to a thin film binding assay result.

26. A device according to claim 22, wherein said light source produces monochromatic electromagnetic radiation.

27. A device according to claim 22, wherein said optical pathway comprises a single polarization element.

28. A device for use in interpreting thin film binding assays, the device comprising:
    a substrate for supporting a sample;
    a light source for producing electromagnetic radiation to illuminate said sample;
    a detector for detecting electromagnetic radiation reflected from said sample, wherein a signal produced by said detector corresponds to the intensity of said reflected electromagnetic radiation;
    an optical pathway between said light source, said sample, and said detector, said optical pathway comprising a single polarization element within said optical pathway, wherein said single polarization element is a fixed polarization element located between said sample and said detector to linearly polarize said reflected electromagnetic radiation; and
    a signal processor for correlating said signal with a film thickness on said sample.

29. A device according to claim 28, wherein said linearly polarized electromagnetic radiation is essentially s-polarized relative to a plane of incidence in said optical pathway between said polarizer and said detector.

30. A device according to claim 28, wherein said linearly polarized electromagnetic radiation is essentially p-polarized relative to a plane of incidence in said optical pathway between said polarizer and said detector.

31. A device according to claim 28, wherein said film thickness is related to a thin film binding assay result.

32. A device according to claim 28, wherein said light source produces monochromatic electromagnetic radiation.

33. A device according to claim 28, wherein said optical pathway comprises a single polarization element.

34. A device for use in interpreting thin film binding assays, the device comprising:
- a substrate for supporting a sample;
- a light source for producing electromagnetic radiation to illuminate said sample;
- a detector for detecting electromagnetic radiation reflected from said sample,
- wherein a signal produced by said detector corresponds to the intensity of said reflected electromagnetic radiation;
- an optical pathway between said light source, said sample, and said detector, said optical pathway not including a polarization element; and
- a signal processor for correlating said signal with a film thickness on said sample.

35. A device according to claim 34, wherein said light source is positioned relative to said sample and said detector to provide a low angle of incidence.

36. A device according to claim 34, wherein said optical pathway comprises neither a polarizer located between said light source and said sample, nor a polarizer located between said sample and said detector.

37. A device according to claim 35, wherein said light source is positioned at an angle of incidence ranging from about 0° to about 30°, determined relative to a line normal to the plane of the sample.

38. A device according to claim 35, wherein said light source is positioned at an angle of incidence ranging from 0° to 20°.

39. A device according to claim 35, wherein said light source is positioned at an angle of incidence ranging from 0° to 10°.

40. A device according to claim 34, wherein said light source produces monochromatic electromagnetic radiation.

41. A device according to claim 34, wherein said film thickness is related to a thin film binding assay result.

42. A device according to claim 34, wherein said optical pathway comprises a polarizing filter which provides circularly polarized light.

43. A device according to claim 42, wherein said polarizing filter is located in said optical pathway between said light source and said sample.

44. A device according to claim 42, wherein said polarizing filter is located in said optical pathway between said sample and said detector.

45. A method of interpreting thin film binding assays, the method comprising:
- providing a device comprising a light source, a detector, a first optical pathway between said light source and a sample, said first optical pathway comprising a fixed polarization element between said light source and said sample, and a second optical pathway between said sample and said detector, said second optical pathway not including a polarization element;
- directing electromagnetic radiation from said light source along said first optical pathway to said sample, whereby electromagnetic radiation is reflected by said sample along said second optical pathway to said detector;
- linearly polarizing said electromagnetic radiation along said first optical pathway at a position prior to contact of said electromagnetic radiation with said sample;
- detecting said electromagnetic radiation reflected by said sample using said detector, whereby a signal is obtained corresponding to the intensity of said reflected electromagnetic radiation; and
- correlating said signal to the film thickness of the sample.

46. The method of claim 45, wherein said linearly polarized electromagnetic radiation is essentially s-polarized relative to a plane of incidence in said second optical pathway between said polarizer and said detector.

47. The method of claim 45, wherein said linearly polarized electromagnetic radiation is essentially p-polarized relative to a plane of incidence in said second optical pathway between said polarizer and said detector.

48. The method of claim 45, wherein said film thickness is related to a thin film binding assay result.

49. The method of claim 45, wherein said light source produces monochromatic electromagnetic radiation.

50. The method of claim 45, wherein said method is performed without polarization of said electromagnetic radiation reflected from said sample.

51. A method of interpreting thin film binding assays, the method comprising:
- providing a device comprising a light source, a detector, a first optical pathway between said light source and a sample, said first optical pathway not including a polarization element, and a second optical pathway between said sample and said detector, said second optical pathway comprising a fixed polarization element between said light source and said sample;
- directing electromagnetic radiation from said light source along said first optical pathway to said sample, whereby electromagnetic radiation is reflected by said sample along said second optical pathway to said detector;
- linearly polarizing said electromagnetic radiation along said second optical pathway at a position after contact of said electromagnetic radiation with said sample;
- detecting said electromagnetic radiation reflected by said sample using said detector, whereby a signal is obtained corresponding to the intensity of said reflected electromagnetic radiation; and
- correlating said signal to the film thickness of the sample.

52. The method of claim 51, wherein said linearly polarized electromagnetic radiation is essentially s-polarized relative to a plane of incidence in said second optical pathway between said polarizer and said detector.

53. The method of claim 51, wherein said linearly polarized electromagnetic radiation is essentially p-polarized relative to a plane of incidence in said second optical pathway between said polarizer and said detector.

54. The method of claim 51, wherein said film thickness is related to a thin film binding assay result.

55. The method of claim 51, wherein said light source produces monochromatic electromagnetic radiation.

56. The method of claim 51, wherein said method is performed without polarization of said electromagnetic radiation prior to reflection from said sample.

57. A method of interpreting thin film binding assays, the method comprising:
- providing a device comprising a light source, a detector, a first optical pathway between said light source and a sample, and a second optical pathway between said sample and said detector, said first and second optical pathways each not including a polarization element;
- directing electromagnetic radiation from said light source along said first optical pathway to said sample, whereby electromagnetic radiation is reflected by said sample along said second optical pathway to said detector, wherein said electromagnetic radiation is unpolarized at said detector without movement of components in said optical pathway;

detecting said electromagnetic radiation reflected by said sample using said detector, whereby a signal is obtained corresponding to the intensity of said reflected electromagnetic radiation; and correlating said signal to the film thickness of the sample.

58. The method of claim 57, wherein said light source is positioned at a low angle of incidence determined relative to a line normal to the sample.

59. The method of claim 57, wherein said optical pathway comprises neither a polarizer located between said light source and said sample, nor a polarizer located between said sample and said detector.

60. The method of claim 58, wherein said low angle of incidence ranges from about 0° to about 30°.

61. The method of claim 58, wherein said low angle of incidence ranges from 0° to 20°.

62. The method of claim 60 wherein said low angle of incidence ranges from 0° to 10°.

63. The method of claim 57, wherein said light source produces monochromatic electromagnetic radiation.

64. The method of claim 57, wherein said film thickness is related to a thin film binding assay result.

65. A device for use in determining a film thickness of a sample, the device comprising:

a substrate for supporting said sample;

a light source for producing electromagnetic radiation to illuminate said sample;

a first polarization element located between said light source and said sample;

a detector for detecting electromagnetic radiation reflected from said sample;

a second polarization element located between said detector and said sample;

a negative control sample; and a data analysis means for utilizing a signal obtained from said detector to determine film thickness, wherein at least one of said first and second polarization elements is a rotatable element which rotates during an operating mode of said device to vary an s and/or p component of said electromagnetic radiation with time, and wherein said data analysis means uses a standard function that correlates film thickness to detector signal intensity.

66. A device according to claim 65, wherein the standard function comprises a normalizing function which relates said detector signal intensity to a comparative detector signal intensity obtained from said negative control sample.

67. A device according to claim 66, wherein the normalizing function is a ratio of said detector signal intensity and said comparative detector signal intensity obtained from said negative control sample.

68. A method of measuring a film thickness of a sample, the method comprising:

providing a device comprising a light source, a polarizer, an analyzer, and a detector;

directing electromagnetic radiation from the light source towards the sample, whereby electromagnetic radiation is reflected from the sample;

polarizing the electromagnetic radiation that is directed towards the sample using the polarizer;

polarizing the electromagnetic radiation reflected from the sample using the analyzer;

rotating the polarizer or the analyzer to vary the s and p content of the polarized electromagnetic radiation with time;

detecting the polarized electromagnetic radiation reflected from the sample using the detector, whereby a signal is obtained corresponding to the intensity of the reflected electromagnetic radiation;

providing a comparative detector signal intensity obtained from a negative control sample; and correlating the signal to the film thickness of the sample, wherein said correlation step comprises using a standard function that relates film thickness to detector signal intensity.

69. The method of claim 68 wherein the standard function comprises a normalizing function which relates the detector signal intensity to the comparative detector signal intensity.

70. The method of claim 69, wherein the normalizing function is a ratio of the detector signal intensity and the comparative detector signal intensity.

* * * * *